United States Patent
Saji et al.

(10) Patent No.: US 10,029,022 B2
(45) Date of Patent: Jul. 24, 2018

(54) NUCLEAR MEDICINE DIAGNOSTIC IMAGING AGENT

(71) Applicants: Kyoto University, Kyoto (JP); ARKRAY, Inc., Kyoto (JP)

(72) Inventors: Hideo Saji, Kyoto (JP); Hiroyuki Kimura, Kyoto (JP); Hirokazu Matsuda, Kyoto (JP); Shuichi Nakanishi, Kyoto (JP)

(73) Assignees: Kyoto University, Kyoto (JP); ARKRAY, Inc., Kyoto (JP)

( * ) Notice: Subject to any disclaimer, the term of this patent is extended or adjusted under 35 U.S.C. 154(b) by 141 days.

(21) Appl. No.: 15/140,572

(22) Filed: Apr. 28, 2016

(65) Prior Publication Data

US 2017/0000912 A1 Jan. 5, 2017

(30) Foreign Application Priority Data

Jul. 3, 2015 (JP) ................................ 2015-134793
Apr. 26, 2016 (JP) ................................ 2016-088445

(51) Int. Cl.
| | | |
|---|---|---|
| A61K 51/04 | (2006.01) | |
| C07B 59/00 | (2006.01) | |
| C07D 471/04 | (2006.01) | |

(52) U.S. Cl.
CPC ...... *A61K 51/0459* (2013.01); *A61K 51/0463* (2013.01); *C07B 59/002* (2013.01); *C07D 471/04* (2013.01)

(58) Field of Classification Search
CPC ................................. A61K 51/00; A61K 51/04
See application file for complete search history.

(56) References Cited

U.S. PATENT DOCUMENTS 6,344,459 B1 2/2002 Bridges et al.

OTHER PUBLICATIONS

Gordon Rewcastle et al. Tyrosine Kinase Inhitibors . . . J. Med. Chem. 1998, 41, 742-751.*
Hai-Feng Chen, Computational Study of the Binding Mode of Epidermal Growth Factor Receptor Kinase Inhibitors, Chem. Biol. Drug. Des, 71, 434-446. (Year: 2008).*

Extended European Search Report issued in corresponding European Patent Application No. 16167782.8 dated Jun. 23, 2016.
Chen, "Computational Study of the Binding Mode of Epidermal Growth Factor Receptor Kinase Inhibitors," Chemical Biology & Drug Design, 71: 434-446 (2008).
Shaul et al., "Novel iodine-124 labeled EGFR inhibitors as potential PET agents for molecular imaging in cancer," Bioorganic & Medicinal Chemistry, 12: 3421-3429 (2004).
Office Action issued in corresponding European Patent Application No. 16167782.8 dated Nov. 10, 2017.
Yeh et al., "Molecular imaging of active mutant L858R EGF receptor (EGFR) kinase-expressing nonsmall cell lung carcinomas using PET/CT," PNAS, 108: 1603-1608 (2011).
Pantaleo et al., "Experimental results and related clinical implications of Pet detection of epidermal growth factor receptor (EGFr) in cancer," Annals of Oncology, 20: 213-226 (2009).
Corcoran et al., "Imaging EGFR and HER2 by PET and SPECT: A Review," Medicinal Research Reviews, 34: 596-643 (2014).
Rewcastle et al., "Tyrosine Kinase Inhibitors. 14. Structure-Activity Relationships for Methyl-amino-Substituted Derivatives of 4-[(3-Bromophenyl)amino]-6-(methylamino)-pyrido[3,4-d]pyrimidine (PD 158780), a Potent and Specific Inhibitor of the Tyrosine Kinase Activity of Receptors for the EGF Family of Growth Factors," Journal of Medicinal Chemistry, 41: 742-751 (1998).
Slobbe et al., "Development of [18F]afatinib as new TKI-PET tracer for EGFR positive tumors," Nuclear Medicine and Biology, 41: 749-757 (2014).
Abourbeh et al., "Identifying erlotinib-sensitive non-small cell lung carcinoma tumors in mice using [11C]erlotinib PET," EJNMMI Research, 5: 1-10 (2015).

* cited by examiner

Primary Examiner — Michael G Hartley
Assistant Examiner — Jagadishwar R Samala
(74) Attorney, Agent, or Firm — Morgan, Lewis & Bockius LLP

(57) ABSTRACT

Provided is a radioactive labeled compound capable of detecting a secondary mutation of an epidermal growth factor receptor, where the compound is represented by Formula (1) or a pharmaceutically acceptable salt thereof, where Y, $L_1$, $R_1$ and $R_2$ are as defined.

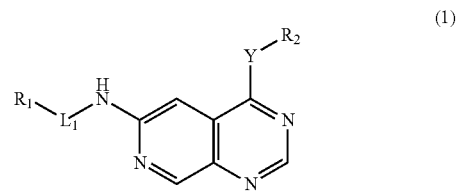

(1)

5 Claims, 3 Drawing Sheets

NUCLEAR MEDICINE DIAGNOSTIC IMAGING AGENT

BACKGROUND OF THE INVENTION

1. Field of the Invention

The present disclosure relates to a radioactive labeled compound with a pyrido[3,4-d]pyrimidine skeleton that can in one aspect provide information for detecting a secondary mutation of an epidermal growth factor receptor (EGFR).

2. Description of Related Art

Lung cancer, which is the number one worldwide cause of death due to cancer, is roughly divided into small cell lung cancer and non-small cell lung cancer according to the histological type thereof. It is known that the EGFR gene that codes for the EGFR, which is a transmembrane tyrosine kinase receptor, has mutated in 10% to 30% of the patients with non-small cell lung cancer that accounts for 80% of lung cancer. The EGFR is activated when mutated and this activation is considered to play a role in cancer growth, etc. Furthermore, once the mutation of the EGFR gene was found, an EGFR-TKI (an epidermal growth factor receptor tyrosine kinase inhibitor), which is a molecular target drug, was considered to be more effective than common anticancer agents. In recent years, therefore, when a patient has been diagnosed as having lung cancer, the possible presence of a mutation in the genes of the patient is checked by a genetic test (for example, Hsin Hsien Yeh et al., PNAS, Jan. 25, 2011; vol. 108, no. 4, 1603-1608). These genetic tests are often carried out using cancer tissue collected by biopsy. However, an invasive biopsy to be attempted on a cancer patient has various risks associated with it and also results in a heavy physical burden. Therefore, there has been a need for new methods that provide alternatives to conventional genetic tests and that avoid various risks associated with the biopsy. As one of the methods, radioactive imaging probes for nuclear medicine diagnosis that can detect EGFR in cancer have been studied (for example, M. A. Pantaleo et al., Annals of Oncology 2009, 20: 213-226; and Emily B. Corcoran et al., Medicinal Research Reviews 2014, 34: 596-643).

Despite the success of the EGFR-TKI, resistance develops within a year and as a result, the EGFR-TKI may no longer provide sufficient therapeutic effects. Since a secondary mutation is considered to play a role in approximately half the cases that develop resistance, it becomes necessary to conduct the genetic test again after the start of treatment with the EGFR-TKI.

SUMMARY OF THE INVENTION

As described above, imaging probes for detecting the EGFR have been studied but a method capable of noninvasively detecting a secondary mutation of the EGFR has not yet been developed. The present disclosure meets this need by providing a radioactive labeled compound capable of detecting a secondary mutation of the EGFR.

In one aspect, the present disclosure relates to a nuclear medicine diagnostic imaging agent comprising a compound represented by Formula (1) described below or a pharmaceutically acceptable salt thereof:

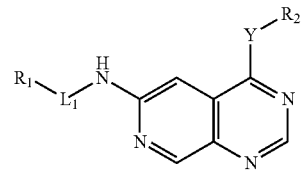

wherein Formula (1), $L_1$ is an alkanediyl group having 1 to 5 carbon atoms or an alkenediyl carbonyl group having 3 to 8 carbon atoms;

$R_1$ is a radioactive halogen atom, or a 5- to 7-membered monocyclic nitrogen-containing heterocycloalkyl that may have one substituent;

$R_2$ is a 6- to 8-membered aryl group or nitrogen-containing heteroaryl group with one substituent;

the substituents of $R_1$ and $R_2$ are each independently a halogen atom, an alkyl group having 1 to 5 carbon atoms, a halogenated alkyl group having 1 to 5 carbon atoms, or a $-(CH_2)_l-(O-C_2H_4)_m-X_1$ group, wherein l is 0 to 5, m is the number of repeating ethyleneoxy groups and is 0 to 5, and $X_1$ is a radioactive halogen atom or $-[^{11}C]CH_3$;

either $R_1$ or $R_2$ contains a radioactive halogen atom or a radioactive carbon atom ($^{11}C$); and Y is $-NH-$ or $-O-$.

In one aspect, the present disclosure relates to a compound represented by Formula (1) described below or a pharmaceutically acceptable salt thereof:

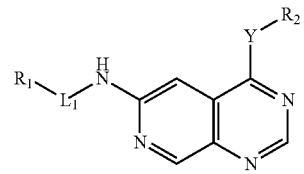

wherein Formula (1), $L_1$ is an alkanediyl group having 1 to 5 carbon atoms or an alkenediyl carbonyl group having 3 to 8 carbon atoms;

$R_1$ is a radioactive halogen atom, or a 5- to 7-membered monocyclic nitrogen-containing heterocycloalkyl that may have one substituent;

$R_2$ is a 6- to 8-membered aryl group or nitrogen-containing heteroaryl group with one substituent;

the substituents of $R_1$ and $R_2$ are each independently a halogen atom, an alkyl group having 1 to 5 carbon atoms, a halogenated alkyl group having 1 to 5 carbon atoms, or a $-(CH_2)_l-(O-C_2H_4)_m-X_1$ group, wherein l is 0 to 5, m is the number of repeating ethyleneoxy groups and is 0 to 5, and $X_1$ is a radioactive halogen atom or $-[^{11}C]CH_3$;

$R_1$ or $R_2$ contains a radioactive halogen atom or a radioactive carbon atom ($^{11}C$); and Y is $-NH-$ or $-O-$.

In one aspect, the present disclosure relates to a labeling precursor composition containing a compound represented by Formula (2) or a pharmaceutically acceptable salt thereof.

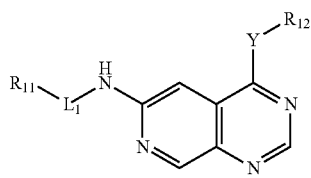

(2)

wherein Formula (2),
$L_1$ is an alkanediyl group having 1 to 5 carbon atoms or an alkenediyl carbonyl group having 3 to 8 carbon atoms;
$R_{11}$ is a chlorine atom, a bromine atom, an iodine atom, or a 5- to 7-membered monocyclic nitrogen-containing heterocycloalkyl that may have one substituent;
$R_{12}$ is a 6- to 8-membered aryl group or nitrogen-containing heteroaryl group with one substituent;
the substituents of $R_{11}$ and $R_{12}$ are each independently a halogen atom, an alkyl group having 1 to 5 carbon atoms, a halogenated alkyl group having 1 to 5 carbon atoms, or a —$(CH_2)_l$—(O—$C_2H_4)_m$—$X_{11}$ group, wherein l is 0 to 5, m is the number of repeating ethyleneoxy groups and is 0 to 5, and $X_{11}$ is a chlorine atom, a bromine atom, an iodine atom, a nitro group, a tosylate group, a mesylate group, a triflate group, a nosylate group, or a brosylate group; and
Y is —NH— or —O—.

In one aspect, the present disclosure relates to a method for obtaining information for evaluating the efficacy of a treatment conducted with an epidermal growth factor receptor tyrosine kinase inhibitor in a subject to be treated for non-small cell lung cancer with the epidermal growth factor receptor tyrosine kinase inhibitor,
wherein the method includes detecting a radioactive signal of a nuclear medicine diagnostic imaging agent of the present disclosure or a compound represented by Formula (1) of the present disclosure from the lung cancer tumor of a subject, to which the nuclear medicine diagnostic imaging agent or the compound or a pharmaceutically acceptable salt thereof was administered.

In one aspect, the present disclosure relates to a method for evaluating the occurrence of a T790M mutation in a gene that codes for an epidermal growth factor receptor present in the lung cancer tumor,
wherein the method includes:
detecting a radioactive signal of a nuclear medicine diagnostic imaging agent of the present disclosure or a compound represented by Formula (1) of the present disclosure from the lung cancer tumor of a subject, to which the nuclear medicine diagnostic imaging agent or the compound or a pharmaceutically acceptable salt thereof was previously administered,
repeating detecting the radioactive signal from the lung cancer tumor of the subject during a treatment conducted with an epidermal growth factor receptor tyrosine kinase inhibitor,
comparing the information thus obtained or the radioactive signals thus detected, and
determining the presence or absence of the occurrence of a T790M mutation in the gene that codes for the epidermal growth factor receptor in the lung cancer tumor, based on variations in the information or signals obtained by the comparison.

In one aspect, the present disclosure relates to a method for evaluating the efficacy of a treatment conducted with an epidermal growth factor receptor tyrosine kinase inhibitor in a subject to be treated for non-small cell lung cancer with the epidermal growth factor receptor tyrosine kinase inhibitor,
wherein the method includes comparing the information obtained by the method for obtaining information of the present disclosure at two or more times selected from the group consisting of a time before starting the administration of the epidermal growth factor receptor tyrosine kinase inhibitor, after starting the administration, and after a lapse of a certain period of time after starting the administration.

In one aspect, the present disclosure can provide a radioactive labeled compound capable of detecting a secondary mutation of an EGFR and a method for evaluating the efficacy of a therapeutic effect of an EGFR-TKI using the same.

DETAILED DESCRIPTION OF THE INVENTION

Figure 1:
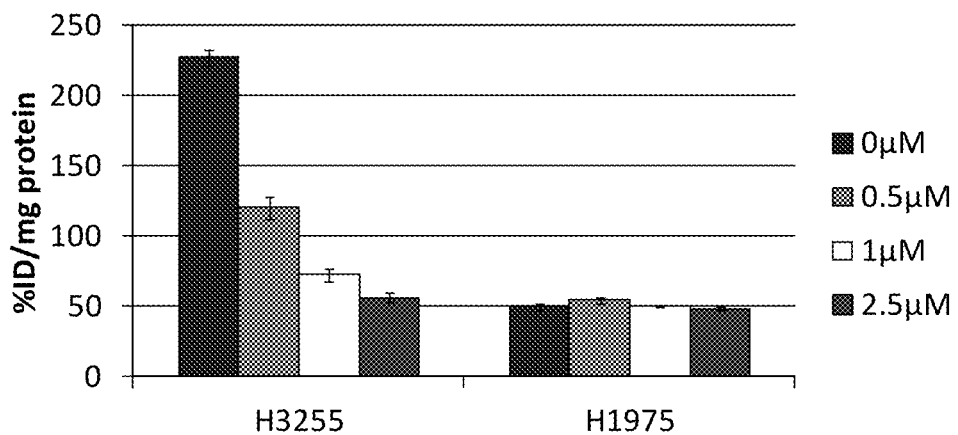
FIG. 1 is a graph showing an example of the results of Experiment 1 on the cellular uptake of [$^{18}$F]H4 using H3255 cells and H1975 cells.

In one aspect, the present disclosure is based on the finding that a compound with a pyrido[3,4-d]pyrimidine skeleton represented by one of Formulae H1 to H4 (Example, Table 1) and synthesized in the examples described herein has a lower binding affinity to L858R/T790M-mutated (double mutant: DM) EGFR as compared to the binding affinity to EGFR, especially, a L858R-mutated EGFR.

Furthermore, in one aspect, the present disclosure is based on the finding that a radioactive halogen-labeled compound with a tetrahydropyridothieno[2,3-d]pyrimidine skeleton, such as a compound [$^{18}$F]H4 ((E)-N-(4-((3-bromophenyl)amino)pyrido[3,4-d]pyrimidin-6-yl)-4-(4-(2-[18F]fluoroethyl)piperazin-1-yl)but-2-enamide), shows a higher adjacent organ rate (for example tumor/muscle, or tumor/blood) in PET imaging of a H3255 tumor-bearing mouse with a L858R-mutated EGFR and shows a significantly lower adjacent organ rate (for example tumor/muscle, or tumor/blood) as compared to that of a H3255 tumor-bearing mouse in PET imaging of a H1975 tumor-bearing mouse with a L858R/T790M-mutated EGFR.

Moreover, in one aspect, the present disclosure is based on the finding that a compound H2 ($N^4$-(3-(2-fluoroethoxy)phenyl)-$N^6$-(2-morpholinoethyl)pyrido[3,4-d]pyrimidine-4, 6-diamine) (Example, Table 1) has a lower binding affinity to a L858R-mutated EGFR as compared to the binding affinity to wild-type EGFR and the binding affinity to a L858R/T790M-mutated EGFR.

In one or more embodiments, a radioactive labeled compound represented by Formula (1) as described herein makes it possible to noninvasively determine whether a T790M mutation, which is a secondary mutation, has developed in the lung cancer tumor in which a mutation that increases the sensitivity of an EGFR-TKI, such as an L858R mutation, has developed in an EGFR gene. Furthermore, in one or more embodiments, a radioactive labeled compound represented by Formula (1) makes it possible to noninvasively determine whether the EGFR-TKI resistance has been acquired in the lung cancer tumor in which a mutation that increases the sensitivity of the EGFR-TKI, such as a L858R mutation, has developed. Moreover, in one or more embodiments, a radioactive labeled compound represented by Formula (1) makes it possible to evaluate the efficacy of a treatment conducted with an EGFR-TKI in a patient with a lung cancer tumor in which a mutation that increases the sensitivity of the EGFR-TKI, such as a L858R mutation, has developed in an EGFR gene.

In one or more embodiments, a compound H2 ($N^4$-(3-(2-fluoroethoxy)phenyl)-$N^6$-(2-morpholinoethyl)pyrido[3,4-d]pyrimidine-4, 6-diamine) makes it possible to noninvasively determine whether an L858R mutation has developed in an EGFR gene.

In one or more embodiments, the term "capable of detecting a secondary mutation of EGFR" in the present specification includes the ability to discriminate an EGFR in which an L858R mutation (a primary mutation) has occurred from an EGFR in which a T790M mutation (a secondary mutation) has occurred in addition to the L858R mutation.

In the present specification, the term "nuclear medicine diagnostic imaging agent" denotes a pharmacological agent containing a radioactive labeled compound that is used for an in vivo nuclear medicine examination in which a compound with a radioactive isotope (RI) bonded thereto is administered to a body and then the radiation (radioactive signals) emitted from the body is measured and imaged from outside the body and thereby, for example, evaluation or examination of the biological function of an organ or a tissue or disease diagnosis is carried out, or a pharmacological agent containing a radioactive labeled compound that is used for an in vitro nuclear medicine examination in which it is reacted with a sample such as a tissue or blood that was sampled from a body and after which, for example, evaluation or examination of the biological function of an organ or a tissue or disease diagnosis is carried out. In one or more embodiments, examples of the in vivo nuclear medicine examination include methods using a nuclear medical imaging probe such as single photon emission computed tomography (SPECT) and positron emission tomography (PET).

In the present specification, the term "pharmaceutically acceptable salt" includes pharmacologically and/or medicinally acceptable salts. Examples thereof include inorganic acid salts, organic acid salts, inorganic base salts, organic base salts, and acidic or basic amino acid salts. In the present disclosure, the term "salt of a compound" can include a hydrate that may be formed when a compound is exposed to the air to absorb moisture. Furthermore, in the present disclosure, the "salt of a compound" can also include a solvate that may be formed when a compound absorbs another solvent of a certain type.

In the present specification, the term "radioactive halogen atom" denotes a radioactive isotope of a halogen atom. Examples of the radioactive halogen atom include, but are not limited to, $^{18}F$, $^{123}I$, $^{124}I$, $^{125}I$, $^{131}I$, $^{75}Br$, $^{76}Br$, and $^{77}Br$. In the present optionally specification, the term "halogen atom" denotes a non-radioactive isotope of a halogen atom. Examples of the halogen atom include a fluorine atom, a chlorine atom, a bromine atom, and an iodine atom.

In the present specification, the term "alkanediyl group having 1 to 5 carbon atoms" denotes a divalent hydrocarbon group having a branched or straight chain of saturated aliphatics containing 1 to 5 carbon atoms in the straight or branched chain. In one or more embodiments, examples of the alkanediyl group having 1 to 5 carbon atoms include a methanediyl group, an ethanediyl group, a propanediyl group, a butanediyl group, and a pentanediyl group.

In the present specification, the term "alkenediyl carbonyl group having 3 to 8 carbon atoms" denotes a divalent hydrocarbon group having one carbonyl group and a branched or straight chain of unsaturated aliphatics with at least one carbon-carbon double bond and containing 2 to 7 carbon atoms in the straight or branched chain. In one or more embodiments, examples of the alkenediyl carbonyl group having 3 to 8 carbon atoms include —(C=O)—CH=CH—, —(C=O)—CH=CH—CH$_2$—, —(C=O)—CH=CH—C$_2$H$_4$—, and —(C=O)—CH=CH—C$_3$H$_6$—.

In the present specification, the term "5- to 7-membered monocyclic nitrogen-containing heterocycloalkyl group" denotes a monocyclic saturated heterocyclic group containing 5 to 7 ring atoms, one or more nitrogen atoms as hetero atoms constituting the ring atoms, and optionally one or more oxygen atoms. In one or more embodiments, examples of the 5- to 7-membered monocyclic nitrogen-containing heterocycloalkyl group include a morpholinyl group, a piperazinyl group, and a piperidinyl group. In the present specification, the term "5- to 7-membered monocyclic nitrogen-containing heterocycloalkyl group that may have one substituent group" denotes a 5- to 7-membered monocyclic nitrogen-containing heterocycloalkyl group having no substituent, or a 5- to 7-membered monocyclic nitrogen-containing heterocycloalkyl group, where one or more carbon atoms or hetero atoms thereof have been substituted.

In the present specification, the term "6- to 8-membered aryl group" denotes a group formed by removing one hydrogen atom from a ring carbon atom of an aromatic hydrocarbon having 6 to 8 carbon atoms. In one or more embodiments, examples of the 6- to 8-membered aryl group include a phenyl group and a naphthyl group. In the present specification, the term "6- to 8-membered nitrogen-containing heteroaryl group" denotes an unsaturated heterocyclic group containing at least 6 to 8 ring atoms and one or more nitrogen atoms as hetero atoms constituting the ring atoms. In one or more embodiments, examples of the 6- to 8-membered nitrogen-containing heteroaryl group include a pyridinyl group and a pyrazinyl group. In the present specification, the term "6- to 8-membered aryl group or the nitrogen-containing heteroaryl group having one substituent" denotes a 6- to 8-membered aryl group or a 6- to 8-membered nitrogen-containing heteroaryl group where a carbon atom or hetero atom thereof has been substituted with one substituent.

In the present specification, the term "alkyl group having 1 to 5 carbon atoms" denotes a monovalent hydrocarbon group having a branched or straight chain of saturated aliphatics containing 1 to 5 carbon atoms in the straight or branched chain. Examples of the alkyl group having 1 to 5 carbon atoms include a methyl group, an ethyl group, a propyl group, an isopropyl group, and a butyl group.

In the present specification, the term "halogenated alkyl group having 1 to 5 carbon atoms" denotes a halogen-substituted alkyl group having 1 to 5 carbon atoms. The term "halogen-substituted alkyl group having 1 to 5 carbon atoms" denotes an alkyl group having 1 to 5 carbon atoms where one or more hydrogen atoms have been substituted with halogen atoms. Examples of the halogen-substituted alkyl group having 1 to 5 carbon atoms include a monofluoromethyl group, a difluoromethyl group, a trifluoromethyl group, a trifluoroethyl group, and a difluoromethylene group.

[Compounds Represented by Formula (1)]

In one or more embodiments, the present disclosure relates to a compound represented by Formula (1) described below or a pharmaceutically acceptable salt thereof (hereinafter referred to as a "compound (1) of the present disclosure"). In one or more embodiments, the compound (1) of the present disclosure exhibits a relatively high binding affinity to L858R-mutated EGFR but no binding affinity to a T790M-mutated EGFR, which is one of the secondary mutations of an EGFR, and a L858R/T790M-mutated EGFR, which is a double mutant (DM).

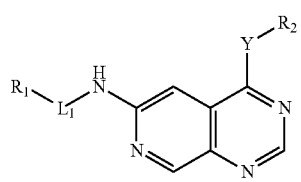

(1)

In Formula (1), Y is —NH— or —O—.

In Formula (1), $L_1$ is an alkanediyl group having 1 to 5 carbon atoms or an alkenediyl carbonyl group having 3 to 8 carbon atoms. In one or more embodiments, examples of $L_1$ include —$(CH_2)_2$— and —(C=O)—CH=CH—$CH_2$—.

In Formula (1), $R_1$ is a radioactive halogen atom, or a 5- to 7-membered monocyclic nitrogen-containing heterocycloalkyl that may have one substituent, $R_2$ is a 6- to 8-membered aryl group or a nitrogen-containing heteroaryl group with one substituent, where the substituents of $R_1$ and $R_2$ are each independently a halogen atom, an alkyl group having 1 to 5 carbon atoms, a halogenated alkyl group having 1 to 5 carbon atoms, or a —$(CH_2)_l$—$(O-C_2H_4)_m$—$X_1$ group; and $R_1$ or $R_2$ contains a radioactive halogen atom or a radioactive carbon atom ($^{11}C$), wherein l is 0, 1, 2, 3, 4, or 5; m is the number of repeating ethyleneoxy groups and is 0, 1, 2, 3, 4, or 5; and $X_1$ is a radioactive halogen atom or —[$^{11}C$]$CH_3$.

In one or more embodiments, examples of $R_1$ include a radioactive halogen atom,

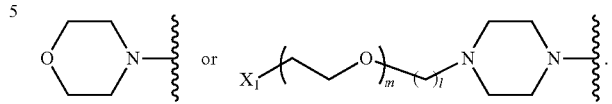

In the case where the compound binds to a L858R-mutated EGFR but has a very low binding affinity to a L858R/T790M-mutated EGFR, $R_1$ is preferably

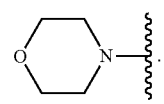

For improving the detection of a secondary mutation of an EGFR, preferably in terms of the fact that a compound has a high binding affinity to a L858R-mutated EGFR and a low binding affinity to a L858R/T790M-mutated EGFR, $R_1$ is preferably

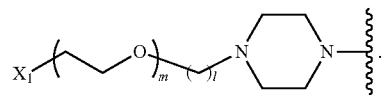

In the above formula, l, m, and $X_1$ are as described above. That is, l is 0, 1, 2, 3, 4, or 5' m is the number of repeating ethyleneoxy groups and is 0, 1, 2, 3, 4, or 5 and $X_1$ is a radioactive halogen atom or —[$^{11}C$]$CH_3$.

In one or more embodiments, $R_2$ is

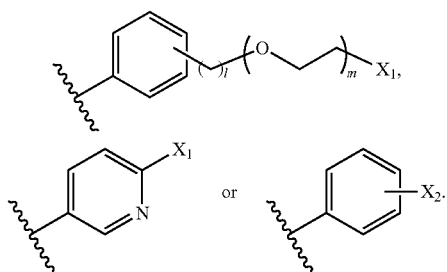

In the formulae, l is 0 or 2, and m is the number of repeating ethyleneoxy groups and is 0, 1, 2, 3, 4, or 5. $X_1$ is a radioactive halogen atom or —[$^{11}C$]$CH_3$. In one or more embodiments, $X_1$ is preferably $^{18}F$ since it can be used as a PET preparation, has a suitable half-life, and has a relatively small atomic size. $X_2$ is a halogen atom, and in one or more embodiments, examples thereof include a bromine atom.

In one or more embodiments, examples of the combinations of $R_1$ and $R_2$ include the combinations shown in the table below.

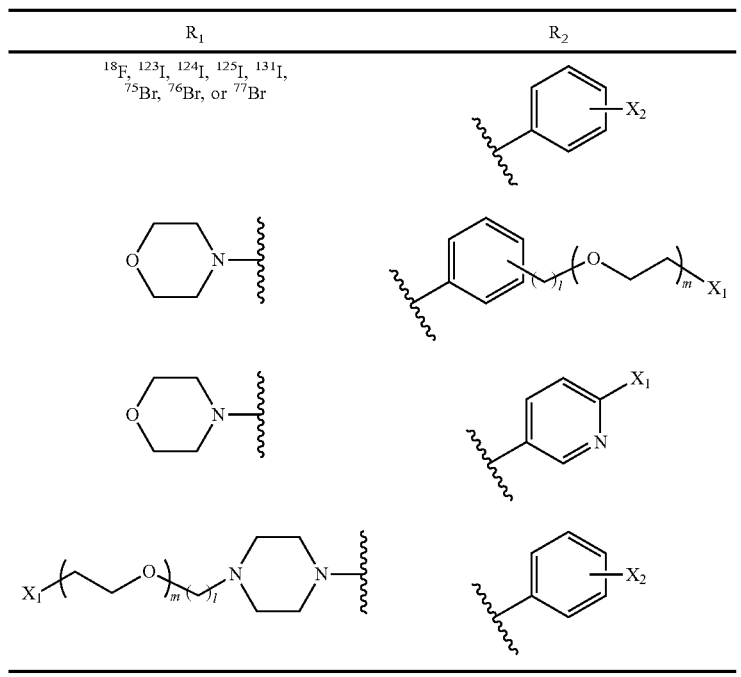

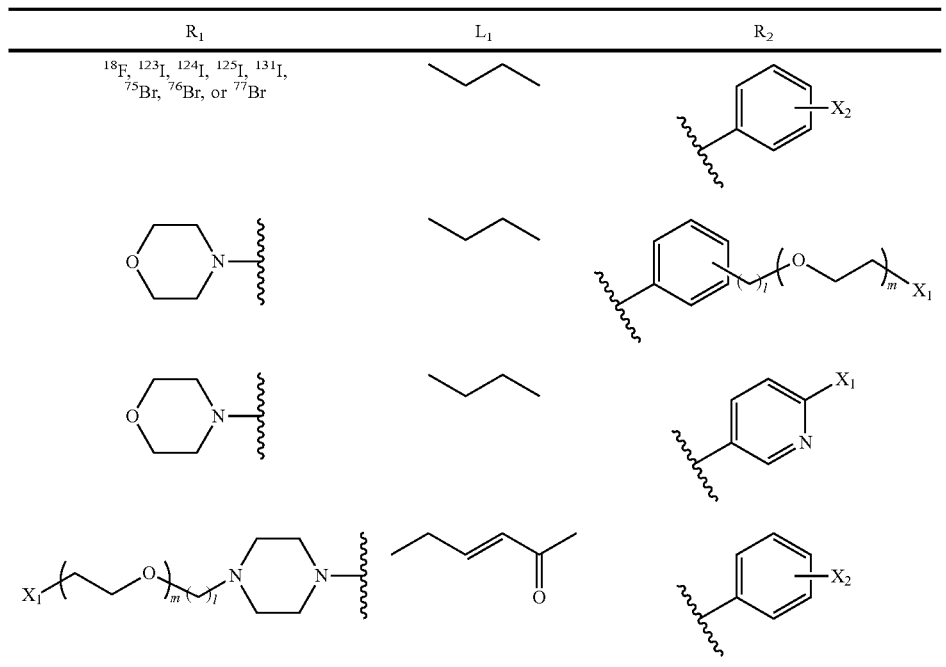

In one or more embodiments, examples of the combinations of $R_1$, $L_1$, and $R_2$ include the combinations shown in the table below.

In one or more embodiments, examples of the compound represented by Formula (1) include compounds represented by Formulae (1-1) to (1-4) described below and pharmaceutically acceptable salts thereof. For improving the detection of a secondary mutation of an EGFR, preferably the compound having a high binding affinity to a L858R-mutated EGFR and a low binding affinity to a L858R/T790M-mutated EGFR is provided, which is preferably a compound represented by Formula (1-1) or (1-4). In the case where a compound which binds to a L858R-mutated EGFR but has a very low binding affinity to a L858R/T790M-mutated EGFR is provided, a compound represented by Formula (1-2) or (1-3) is preferred. In the case where the compound, which while having a low binding affinity to a wild-type EGFR, binds to a L858R-mutated EGFR and has very low binding affinity to a L858R/T790M-mutated EGFR, is provided, a compound represented by Formula (1-2) is preferred. In Formulae (1-1) to (1-4), $X_1$ is a radioactive halogen atom or —[$^{11}$C]CH$_3$, preferably a [$^{18}$F]

fluorine atom. $X_2$ is a halogen atom, preferably a bromine atom.

(1-1)

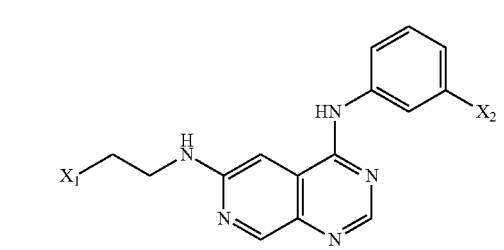

(1-2)

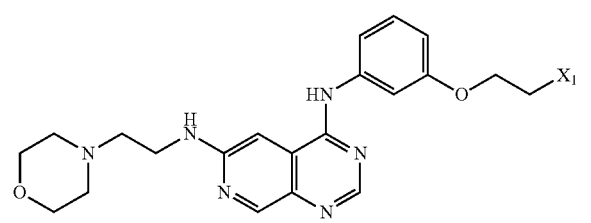

(1-3)

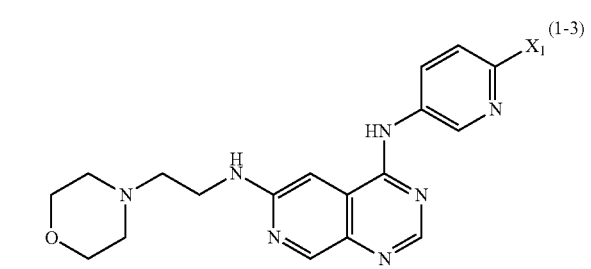

(1-4)

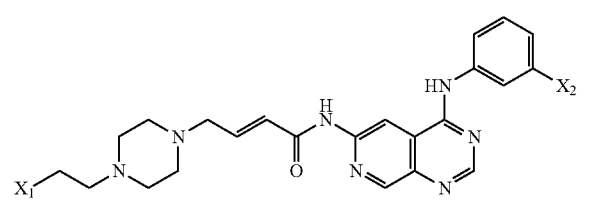

In one or more embodiments, the compound (1) of the present disclosure can be used as an imaging probe, a composition for imaging, a nuclear medicine diagnostic imaging agent (each of which is used for detecting the development of a secondary mutation of EGFR), a diagnostic agent for evaluating the acquisition of an EGFR-TKI resistance, or a diagnostic agent for evaluating the efficacy of a treatment conducted with an EGFR-TKI, in a lung cancer tumor, in which a mutation that increases the sensitivity of an EGFR-TKI such as a L858R mutation has developed, or in a patient with said tumor. In one or more embodiments, therefore, the present disclosure relates to an imaging probe, a composition for imaging, a nuclear medicine diagnostic imaging agent, a diagnostic agent for evaluating the acquisition of an EGFR-TKI resistance, or a diagnostic agent for evaluating the efficacy of a treatment conducted with an EGFR-TKI, each of which contains a compound represented by Formula (1) or a pharmaceutically acceptable salt thereof. In one or more embodiments, the present disclosure relates to an imaging probe, a composition for imaging, a nuclear medicine diagnostic imaging agent, a diagnostic agent for evaluating the acquisition of an EGFR-TKI resistance, or a diagnostic agent for evaluating the efficacy of a treatment conducted with an EGFR-TKI, each of which contains, as an active ingredient, a compound represented by Formula (1) or a pharmaceutically acceptable salt thereof.

In the present disclosure, the form of the composition for imaging and the various diagnostic agents is not particularly limited but in one or more embodiments, examples of the form include a solution and powder. They may contain pharmaceutical additives such as a carrier.

[Method for Preparing Compound Represented by Formula (1)]

In one or more embodiments, the compound (1) of the present disclosure can be produced by radioactively labeling a compound represented by Formula (2) described below or a pharmaceutically acceptable salt thereof. In one or more embodiments, therefore, the present disclosure relates to a method for preparing a radioactive compound, including radioactively labeling a compound represented by Formula (2) or a pharmaceutically acceptable salt thereof. Furthermore, in one or more embodiments, the present disclosure relates to a method for preparing a compound represented by Formula (1) including radioactively labeling a compound represented by Formula (2) or a pharmaceutically acceptable salt thereof.

(2)

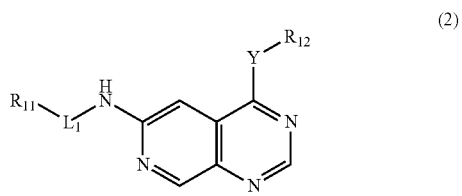

In Formula (2), Y is —NH— or —O—.

In Formula (2), $L_1$ is an alkanediyl group having 1 to 5 carbon atoms or an alkenediyl carbonyl group having 3 to 8 carbon atoms. Examples of $L_1$ include those described above.

In Formula (2), $R_{11}$ is a chlorine atom, a bromine atom, an iodine atom, or a 5- to 7-membered monocyclic nitrogen-containing heterocycloalkyl that may have one substituent.

In Formula (2), $R_{12}$ is a 6- to 8-membered aryl group or a nitrogen-containing heteroaryl group with one substituent.

The substituents of $R_{11}$ and $R_{12}$ are each independently a halogen atom, an alkyl group having 1 to 5 carbon atoms, a halogenated alkyl group having 1 to 5 carbon atoms, or a —$(CH_2)_l$—$(O-C_2H_4)_m$—$X_{11}$ group, wherein l is 0 to 5, m is the number of repeating ethyleneoxy groups and is 0 to 5, and $X_{11}$ is a chlorine atom, a bromine atom, an iodine atom, a nitro group, a tosylate group, a mesylate group, a triflate group, a nosylate group, or a brosylate group.

In one or more embodiments, $R_{11}$ is, for example,

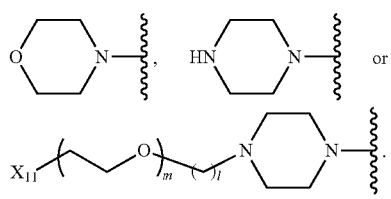

In the case where the compound binds to L858R-mutated EGFR but has a very low binding affinity to L858R/T790M-mutated EGFR, $R_{11}$ is preferably

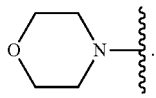

In the case where the compound has a high binding affinity to L858R-mutated EGFR, $R_{11}$ is preferably

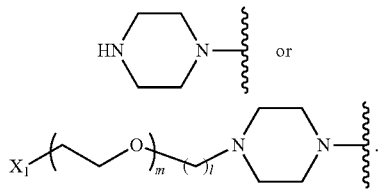

In the above formulae, l, m, and $X_{11}$ are as described above. That is, l is 0 to 5, m is the number of repeating ethyleneoxy groups and is 0 to 5, and $X_{11}$ is a chlorine atom, a bromine atom, an iodine atom, a nitro group, a tosylate group, a mesylate group, a triflate group, a nosylate group, or a brosylate group.

In one or more embodiments, $R_{12}$ is

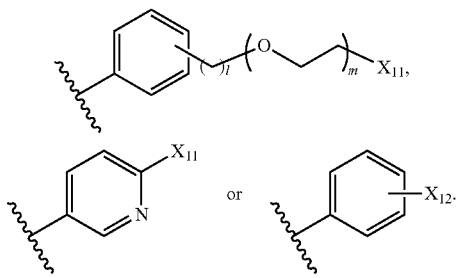

In the above formulae, l is 0 or 2, and m is the number of repeating ethyleneoxy groups and is 0, 1, 2, 3, 4, or 5. $X_{11}$ is a chlorine atom, a bromine atom, an iodine atom, a nitro group, a tosylate group, a mesylate group, a triflate group, a nosylate group, or a brosylate group, and $X_{12}$ is a chlorine atom, a bromine atom, or an iodine atom.

In one or more embodiments, examples of the combination of $R_{11}$ and $R_{12}$ include the combinations shown in the table below.

| $R_{11}$ | $R_{12}$ |
|---|---|
| Br, I, Cl, or $NO_2$ | ![](X12 phenyl) |
| | l-O-(CH2CH2O)m-X11) |
| | |
| ![](piperazine HN) | ![](X12 phenyl) |
| m-(CH2)l-piperazine) | ![](X12 phenyl) |

In one or more embodiments, examples of the combination of $R_{11}$, $L_1$, and $R_{12}$ include the combinations shown in the table below.

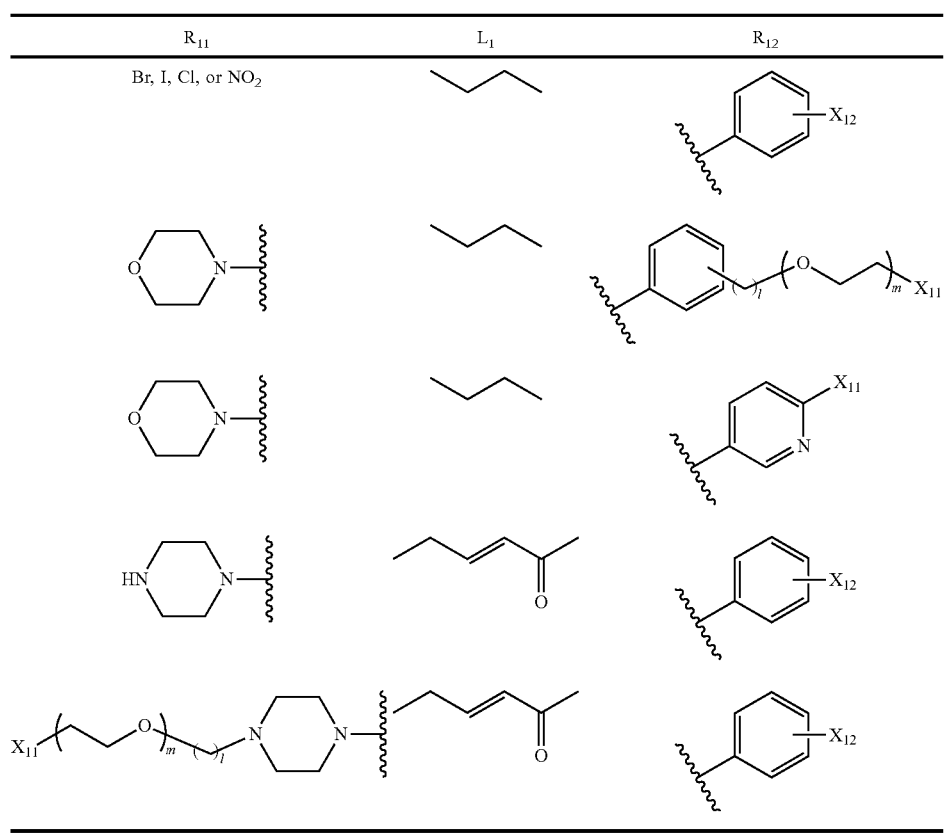

In one or more embodiments, examples of the compound represented by Formula (2) include compounds represented by Formulae (2-1) to (2-5) described below and pharmaceutically acceptable salts thereof. For improving the detection of the secondary mutation of EGFR, preferably in terms of the fact that a compound having a high binding affinity to L858R-mutated EGFR and a low binding affinity to L858R/T790M-mutated EGFR is provided, which is preferably a compound represented by Formula (2-1), (2-4), or (2-5). In the case where the compound which binds to L858R-mutated EGFR but has a very low binding affinity to L858R/T790M-mutated EGFR is provided, a compound represented by Formula (2-2) or (2-3) is preferred. In Formulae (2-1) to (2-5), $X_{11}$ is a chlorine atom, a bromine atom, an iodine atom, a nitro group, a tosylate group, a mesylate group, a triflate group, a nosylate group, or a brosylate group. $X_{12}$ is a halogen atom, preferably a bromine atom.

(2-1)

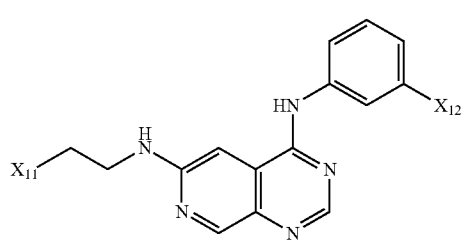

-continued (2-2)

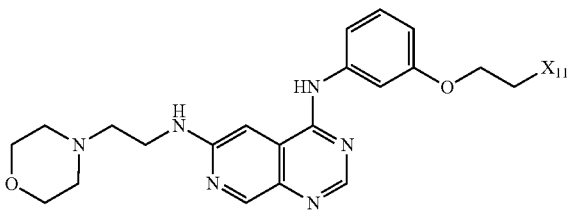

(2-3)

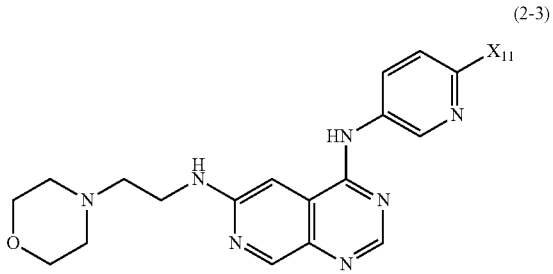

(2-4)

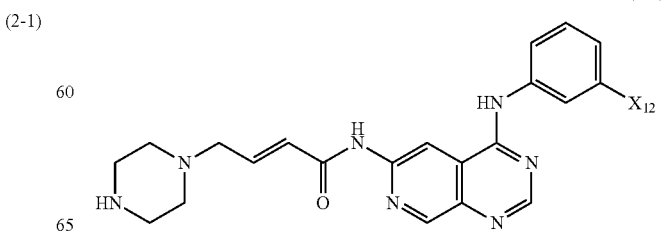

-continued (2-5)

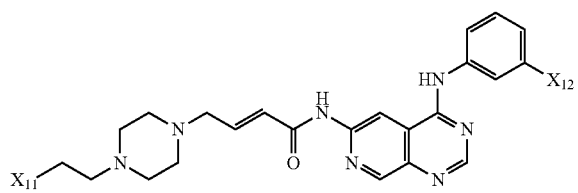

The method for radioactively labeling a compound represented by Formula (2) can be determined suitably according to the compound represented by Formula (2). In one or more embodiments, when Formula (2) contains $X_{11}$, the compound can be labeled using a direct labeling method. When $R_{11}$ is

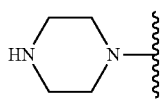

as shown in Formula (2-4), for example, $X_{11}$—$(CH_2)_l$—$(O-C_2H_4)_m$—$X_1$ can be used to label the compound using an indirect labeling method. $X_1$, $X_{11}$, l, and m are as described above. That is, $X_1$ is a radioactive halogen atom or —[$^{11}$C]CH$_3$, $X_{11}$ is a chlorine atom, a bromine atom, an iodine atom, a nitro group, a tosylate group, a mesylate group, a triflate group, a nosylate group, or a brosylate group, l is 0 to 5, and m is the number of repeating ethyleneoxy groups and is 0 to 5.

As described above, the compound represented by Formula (2) can be used as a labeling precursor (i.e., an unlabeled compound used for a radioactive labeling). In one or more embodiments, therefore, the present disclosure relates to a compound represented by Formula (2) or a pharmaceutically acceptable salt thereof (hereinafter referred to as a "compound (2) of the present disclosure"). Furthermore, in one or more embodiments, the present disclosure relates to a composition containing a compound (2) of the present disclosure that is used as a labeling precursor for synthesizing a compound (1) of the present disclosure. Moreover, in one or more embodiments, the present disclosure relates to a kit for preparing a compound (1) of the present disclosure containing a compound (2) of the present disclosure. In one or more embodiments, the kit of the present disclosure may further include a labeling reagent containing a radioactive halogen atom.

[Method for Obtaining Information or Data for Evaluating Efficacy of Treatment Conducted with an EGFR-TKI]

In one or more embodiments, the present disclosure relates to a method for obtaining information or data for evaluating the efficacy of a treatment conducted with an EGFR-TKI in a subject to be treated for non-small cell lung cancer with the EGFR-TKI (hereinafter also referred to as a "method for obtaining information of the present disclosure"). The subject is not particularly limited but in one or more embodiments, the subject is selected from human beings, mammals other than human beings, cultured cells, and subjects in which EGFR may exist.

In one or more embodiments, the method for obtaining information of the present disclosure includes detecting a radioactive signal of a compound (1) of the present disclosure or a nuclear medicine diagnostic imaging agent containing a compound (1) of the present disclosure from a lung cancer tumor of a subject, to which the compound (1) of the present disclosure or the nuclear medicine diagnostic imaging agent has been administered. The method for detecting the signal can be suitably determined according to the type of the radioisotope contained in the compound of the present disclosure to be used and can be carried out using, for example, PET or SPECT. In one or more embodiments, examples of the information or data include radioactive signals that are detected.

In one or more embodiments, the method for obtaining information of the present disclosure includes repeating detecting the radioactive signal from the lung cancer tumor of the subject during the treatment conducted with an EGFR-TKI.

In one or more embodiments, examples of the EGFR-TKI to be used for the treatment include a reversible EGFR-TKI. In one or more embodiments, examples of the reversible EGFR-TKI include gefitinib and erlotinib.

[Method for Evaluating Efficacy of Treatment Conducted with an EGFR-TKI]

In one or more embodiments, the present disclosure relates to a method for evaluating the efficacy of a treatment conducted with an EGFR-TKI in a subject to be treated for non-small cell lung cancer with the EGFR-TKI (hereinafter also referred to as an "evaluation method of the present disclosure").

In one or more embodiments, the evaluation method of the present disclosure includes comparing the information or data obtained by the method for obtaining information of the present disclosure at two or more times selected from the group consisting of the time before starting the administration of an EGFR-TKI, the time after starting the administration, and the time after a lapse of a certain period of time after starting the administration.

In one or more embodiments, the evaluation method of the present disclosure may include determining, based on variations in the signals obtained by the comparison, whether a T790M mutation has been developed in a gene that codes for the epidermal growth factor receptor in lung cancer tumor. Furthermore, in one or more embodiments of the evaluation method of the present disclosure, when a reduction in the signals is observed by the comparison, it can be determined that the possibility of the efficacy of the treatment conducted with an EGFR-TKI is reduced, while when a reduction in the signals is not observed by the comparison, it can be determined that the possibility of the pharmacological efficacy of the treatment conducted with an EGFR-TKI exists. Furthermore, in one or more embodiments of the evaluation method of the present disclosure, when the size of the tumor increases or is maintained while the reduction in the signals is observed, it can be determined that the possibility of the pharmacological efficacy of the treatment conducted with the EGFR-TKI is reduced.

In one or more embodiments, the evaluation method of the present disclosure may include obtaining a CT or MRI image of the subject and fusing the CT or MRI image and an imaging picture constructed from the radioactive signals detected above or comparing them with each other. Furthermore, in one or more embodiments of the evaluation method of the present disclosure, based on the above-mentioned fusion or comparison, when the size of the tumor increases or is maintained while the reduction in the signals is observed, it can be determined that the possibility of the pharmacological efficacy of the treatment conducted with an EGFR-TKI is reduced.

[Method for Imaging EGFR-Positive Lung Cancer Tumor]

In one or more embodiments, the present disclosure relates to an imaging method including detecting a radioactive signal of a compound (1) of the present disclosure from a subject, to which the compound has been administered.

[Compound Represented by Formula (3)]

In one or more embodiments, the present disclosure relates to compounds represented by Formulae (3-1) to (3-5) described below or pharmaceutically acceptable salts thereof.

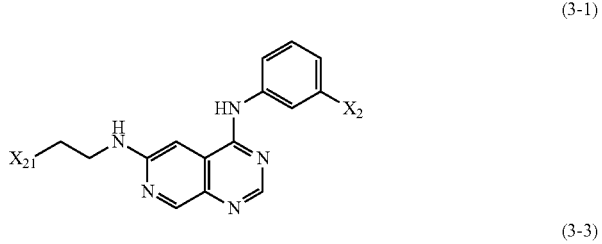

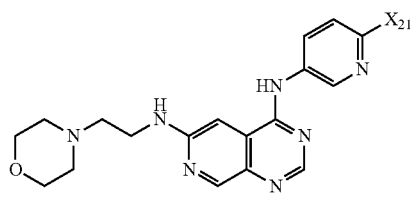

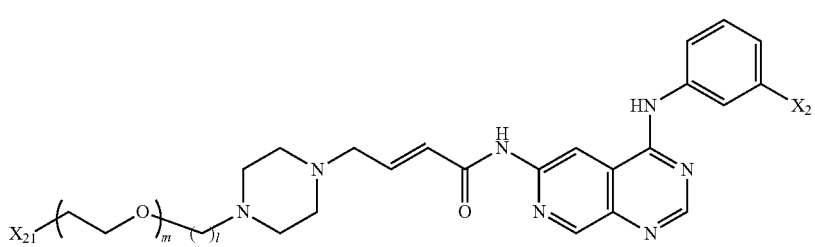

In the formulae above, $X_{21}$ is a halogen atom, preferably a fluorine atom; $X_2$ is a halogen atom, preferably a bromine atom; l is 0, 1, 2, 3, 4, or 5, preferably 0 or 2; and m is the number of repeating ethyleneoxy groups and is 0, 1, 2, 3, 4, or 5, preferably 0 or 3.

The present disclosure may relate to one or more embodiments described below.

<1> A nuclear medicine diagnostic imaging agent, including a compound represented by Formula (1) described below or a pharmaceutically acceptable salt of a compound represented by Formula (1).

(1)

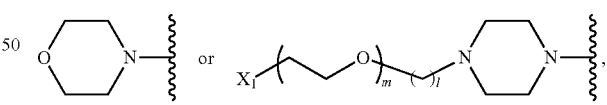

In Formula (1),
$L_1$ is an alkanediyl group having 1 to 5 carbon atoms or an alkenediyl carbonyl group having 3 to 8 carbon atoms,
$R_1$ is a radioactive halogen atom, or a 5- to 7-membered monocyclic nitrogen-containing heterocycloalkyl that may have one substituent,
$R_2$ is a 6- to 8-membered aryl group or nitrogen-containing heteroaryl group with one substituent, the substituents of $R_1$ and $R_2$ are each independently a halogen atom, an alkyl group having 1 to 5 carbon atoms, a halogenated alkyl group having 1 to 5 carbon atoms, or a $-(CH_2)_l-(O-C_2H_4)_m-X_1$ group, wherein l is 0 to 5, m is the number of repeating ethyleneoxy groups and is 0 to 5, and $X_1$ is a radioactive halogen atom or $-[^{11}C]CH_3$, $R_1$ or $R_2$ contains a radioactive halogen atom or a radioactive carbon atom ($^{11}C$), and Y is $-NH-$ or $-O-$.

<2> The nuclear medicine diagnostic imaging agent according to the item <1>, wherein $L_1$ is $-(CH_2)_2-$ or $-(C=O)-CH=CH-CH_2-$.

<3> The nuclear medicine diagnostic imaging agent according to the item <1> or <2>, wherein $R_1$ is

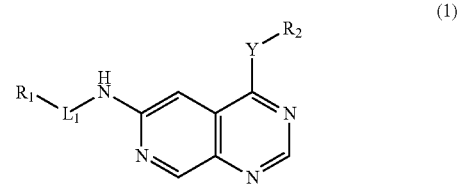

wherein l is 0 or 2, m is the number of repeating ethyleneoxy groups and is 0 to 5, and $X_1$ is a radioactive halogen atom or $-[^{11}C]CH_3$.

<4> The nuclear medicine diagnostic imaging agent according to any one of the items <1> to <3>, wherein $R_2$ is

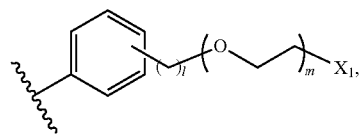

-continued

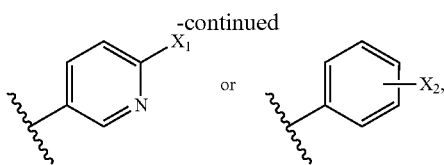

wherein l is 0 or 2, m is the number of repeating ethyleneoxy groups and is 0 to 5, $X_1$ is a radioactive halogen atom or —[$^{11}$C]CH$_3$, and $X_2$ is a halogen atom.

<5> A compound represented by Formula (1) described below or a pharmaceutically acceptable salt of a compound represented by Formula (1).

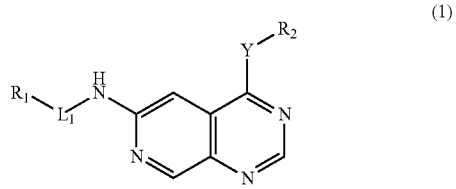

In Formula (1),
$L_1$ is an alkanediyl group having 1 to 5 carbon atoms or an alkenediyl carbonyl group having 3 to 8 carbon atoms,
$R_1$ is a radioactive halogen atom, or a 5- to 7-membered monocyclic nitrogen-containing heterocycloalkyl that may have one substituent,
$R_2$ is a 6- to 8-membered aryl group or a nitrogen-containing heteroaryl group with one substituent,
the substituents of $R_1$ and $R_2$ are each independently a halogen atom, an alkyl group having 1 to 5 carbon atoms, a halogenated alkyl group having 1 to 5 carbon atoms, or a —(CH$_2$)$_l$—(O—C$_2$H$_4$)$_m$—X$_1$ group, wherein l is 0 to 5, m is the number of repeating ethyleneoxy groups and is 0 to 5, and $X_1$ is a radioactive halogen atom or —[$^{11}$C]CH$_3$,
$R_1$ or $R_2$ contains a radioactive halogen atom or a radioactive carbon atom ($^{11}$C), and
Y is —NH— or —O—.

<6> A labeling precursor composition containing a compound represented by Formula (2) described below or a pharmaceutically acceptable salt of a compound represented by Formula (2).

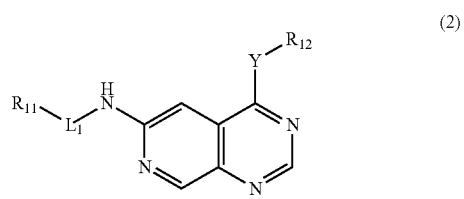

In Formula (2),
$L_1$ is an alkanediyl group having 1 to 5 carbon atoms or an alkenediyl carbonyl group having 3 to 8 carbon atoms,
$R_{11}$ is a chlorine atom, a bromine atom, an iodine atom, or a 5- to 7-membered monocyclic nitrogen-containing heterocycloalkyl that may have one substituent,
$R_{12}$ is a 6- to 8-membered aryl group or nitrogen-containing heteroaryl group with one substituent,
the substituents of $R_{11}$ and $R_{12}$ are each independently a halogen atom, an alkyl group having 1 to 5 carbon atoms, a halogenated alkyl group having 1 to 5 carbon atoms, or a —(CH$_2$)$_l$—(O—C$_2$H$_4$)$_m$—X$_{11}$ group, wherein l is 0 to 5, m is the number of repeating ethyleneoxy groups and is 0 to 5, and $X_{11}$ is a chlorine atom, a bromine atom, an iodine atom, a nitro group, a tosylate group, a mesylate group, a triflate group, a nosylate group, or a brosylate group, and
Y is —NH— or —O—.

<7> The composition according to the item <6>, wherein $L_1$ is —(CH$_2$)$_2$— or —(C═O)—CH═CH—CH$_2$—.

<8> The composition according to the item <6> or <7>, wherein $R_{11}$ is

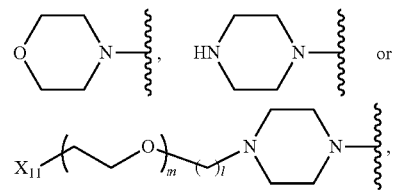

wherein l is 0 to 5, m is the number of repeating ethyleneoxy groups and is 0 to 5, and $X_{11}$ is a chlorine atom, a bromine atom, an iodine atom, a nitro group, a tosylate group, a mesylate group, a triflate group, a nosylate group, or a brosylate group.

<9> The composition according to any one of the items <6> to <8>, wherein $R_{12}$ is

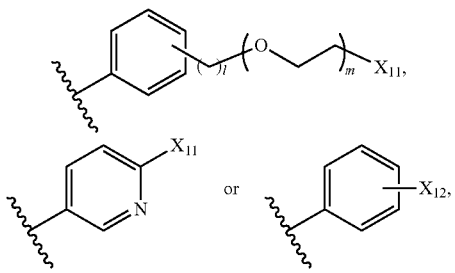

wherein l is 0 or 2, m is the number of repeating ethyleneoxy groups and is 1 to 5, $X_{11}$ is a chlorine atom, a bromine atom, an iodine atom, a nitro group, a tosylate group, a mesylate group, a triflate group, a nosylate group, or a brosylate group, and $X_{12}$ is a halogen atom.

<10> A method for obtaining information or data for evaluating the efficacy of a treatment conducted with an EGFR-TKI in a subject to be treated for non-small cell lung cancer with the EGFR-TKI,
wherein the method includes detecting a radioactive signal of a nuclear medicine diagnostic imaging agent according to any one of the items <1> to <4> or a compound according to the item <5> from the lung cancer tumor of the subject, to which the nuclear medicine diagnostic imaging agent or the compound or a pharmaceutically acceptable salt thereof was administered.

<11> The method according to the item <10>, wherein the method includes repeating detecting the radioactive signal from the lung cancer tumor of the subject during the treatment conducted with the EGFR-TKI.

<12> A method for evaluating the occurrence or development of a T790M mutation in a gene that codes for an EGFR in a lung cancer tumor,
wherein the method includes:
detecting a radioactive signal of a nuclear medicine diagnostic imaging agent according to any one of the items <1> to <4> or a compound according to the item <5> from the lung cancer tumor of a subject, to which the nuclear medicine diagnostic imaging agent or the compound or a pharmaceutically acceptable salt thereof was administered, repeating detecting the radioactive signal from the lung cancer tumor of the subject during a treatment conducted with an EGFR-TKI, comparing the information or data thus obtained, and determining the presence or absence of the occurrence or development of a T790M mutation in the gene that codes for the EGFR in the lung cancer tumor, based on variations in the signals obtained by the comparison.

<13> A method for evaluating the efficacy of a treatment conducted with an EGFR-TKI in a subject to be treated for non-small cell lung cancer with the EGFR-TKI, wherein the method includes comparing information or data obtained by a method according to the item <10> or <11> at two or more timings selected from the group consisting of those before starting the administration of the EGFR-TKI, after starting the administration, and after a lapse of a certain period of time after starting the administration.

<14> The method according to the item <13>, wherein the method includes determining, based on variations in the signals obtained by the comparison, whether a gene that codes for an EGFR in a lung cancer tumor has a T790M mutation.

<15> The method according to the item <13>, wherein when a reduction in the signals is observed by the comparison, it is determined that the possibility of the pharmacological efficacy of the treatment conducted with the EGFR-TKI is reduced, while when a reduction in the signals is not observed by the comparison, it is determined that the possibility of the pharmacological efficacy of the treatment conducted with the EGFR-TKI exists.

<16> The method according to any one of the items <13> to <15>, wherein when the size of the tumor increases or is maintained while the reduction in the signals is observed, it is determined that the possibility of the pharmacological efficacy of the treatment conducted with the EGFR-TKI is reduced.

<17> The method according to any one of the items <13> to <16>, wherein the method includes:

imaging a CT or MRI image of the subject, and fusing the CT or MRI image and an imaging picture constructed from the radioactive signals that have been detected or comparing them with each other, and based on the fusion or comparison, when the size of the tumor increases or is maintained while the reduction in the signals is observed, it is determined that the possibility of the pharmacological efficacy of the treatment conducted with the EGFR-TKI is reduced.

EXAMPLES

Hereinafter, the present disclosure is further described by way of examples. However, they are illustrative and the present disclosure shall not be interpreted to be limited to the following examples.

[Apparatuses and Reagents]

Mass spectrometry (ESI-MS) was measured with LCMS-2010 EV (Shimadzu Corporation).

$^1$H (400 MHz) NMR spectrum was measured with LNM-AL 400 (JEOL Ltd.), and tetramethylsilane was used as an internal standard substance.

LC-20AD (Shimadzu Corporation) was used for reversed-phase HPLC, and SPD-20A UV (Shimadzu Corporation) was used as a detector. The reversed-phase HPLC columns used herein were COSMOSIL C18-AR-II (4.6×250 mm) and COSMOSIL C18-AR-II (10×250 mm) (Nacalai Tesque, Inc.), and the mobile phases used herein were (A) a 0.1% TFA aqueous solution, (B) a 0.1% TFA acetonitrile solution, (C) a 0.01M citrate buffer solution (pH 4.6), and (D) methanol. Silica gel 60 F254 (Merck Ltd., Japan) was used for TLC. Amino-silica gel preparative TLC was used for PTLC.

An intermediate pressure column W-Prep 2XY (Yamazen Corporation) was used for purification by column chromatography, and the silica gel used herein was Hi Flash silica gel 40 mm, 60 Å (Yamazen Corporation).

[$^{18}$F]fluoride was produced using [$^{18}$O]H$_2$O (Taiyo Nippon Sanso Corporation) and CYPRIS HM-18 Cyclotron (Sumitomo Heavy Industries, Ltd.) installed at Kyoto University Hospital.

A microwave reactor (Saida FDS Inc.) was used to synthesize radioactive compounds. Radioactivity was measured using a curie-meter IGC-7 (ALOKA) and an auto well gamma counter Wallac 1480 WIZARD 3 (PerkinElmer).

Image acquisition by a PET device was carried out using a GMI FX-3300 Pre-Clinical Imaging System.

[Synthesis of Compounds]

H1 to H4 were synthesized. Compounds 1, 6, and 10 were synthesized according to G. W. Rewcastle, D. K. Murray, W. L. Elliott, D. W. Fry, C. T. Howard, J. M. Nelson, B. J. Roberts, P. W. Vincent, H. D. H. Showalter, R. T. Winters, W. A. Denny, *J. Med. Chem.* 1998, 41, 742-751.

Production Example 1

Synthesis of 4-[(3-Bromophenyl)amino]-6-(2-fluoroethylamino)pyrido[3,4-d]pyrimidine (H1)

H1 was synthesized according to the following scheme.

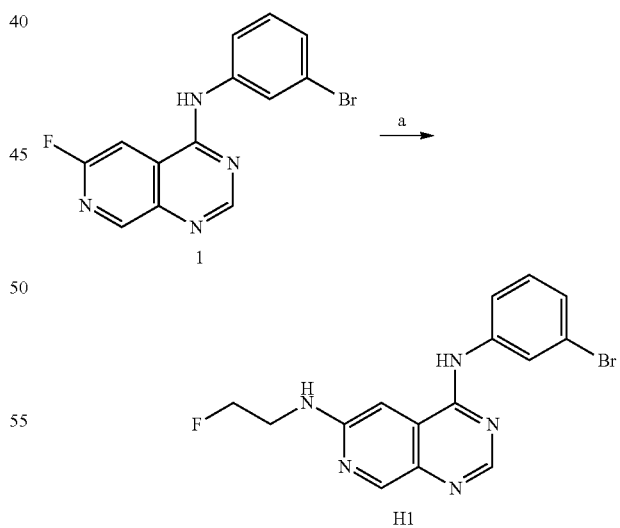

(a) tert-butyl 4-(2-aminoethyl)piperazine-1-carboxylate, Et3N in DMSO, 80° C.

Compound 1 (79.8 mg, 0.250 mmol) was dissolved in DMSO (3 mL), Et$_3$N (697 μL, 5.00 mmol) and 2-fluoroethylamine hydrochloride (498 mg, 5.00 mmol) were added thereto, which then was stirred at 80° C. for 16 hours. After completion of the reaction, the reaction solution was poured into water and then was extracted with ethyl acetate. The organic layer thus obtained was washed with water and brine sequentially and then was dried with sodium sulfate. Thereafter, the solvent was evaporated to dryness. The residue thus obtained was purified by silica gel preparative TLC (CHCl$_3$/MeOH=10/1). Yield 7.9 mg (9%), $^1$H NMR (400 MHz, DMSO-d$_6$) δ9.69 (1H, s), 8.77 (1H, s), 8.41 (1H, s), 8.19 (1H, t, J=2.2 Hz), 7.90 (1H, br d, J=8.8 Hz), 7.37 (1H, t, J=8.1 Hz), 7.32-7.30 (1H, m), 7.19 (1H, s), 6.96 (1H, t, J=6.1 Hz), 4.64 (2H, dt, J=47.6, 5.5 Hz), 3.66 (2H, dq, J=24.9, 5.5 Hz)

Production Example 2

Synthesis of N$^4$-(3-(2-fluoroethoxy)phenyl)-N$^6$-(2-morpholinoethyl)pyrido[3,4-d]pyrimidine-4, 6-diamine (H2)

H2 was synthesized according to the following scheme.

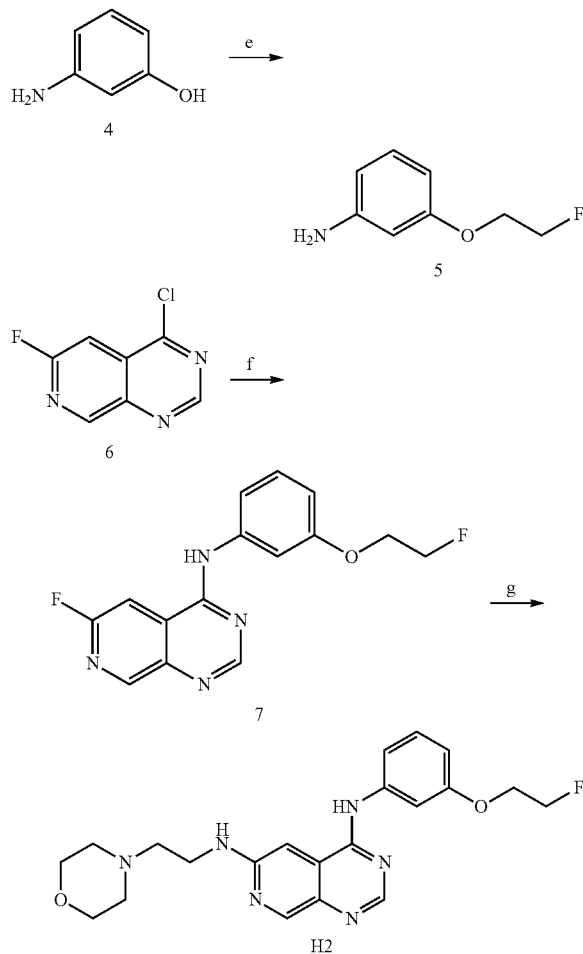

(e) 2-fluoroethyl-4-toluene sulfonate, K2CO3 in DMF, 70° C.; (f) 5 in 2-propanol, reflux; (g) 5-amino-2-fluoropyridine in 2-propanol, reflux;

3-(2-Fluoroethoxy)aniline (Compound 5)

Compound 4 (1.375 mmol, 1.0 eq) was dissolved in DMF (2.0 mL) and K$_2$CO$_3$ (2.749 mmol, 2.0 eq) and 2-fluoroethyl-4-toluene sulfonate (1.649 mmol, 1.2 eq) were added thereto, which then was heated overnight at 70° C. The reaction solution was extracted with ethyl acetate and then the organic layer was collected, which was dried with sodium sulfate. Thereafter, the solvent was evaporated to dryness. The residue was purified by column chromatography and thus Compound 5 was obtained.

Yield 140.1 mg (65.7%), $^1$H NMR (400 MHz, CDCl$_3$) δ7.06 (1H, t, J=8.0 Hz), 6.32 (2H, m), 6.27 (1H, t, J=2.0 Hz), 6.27 (1H, t, J=2.0 Hz), 4.73 (2H, dt, J=47.6, 4.0 Hz), 4.17 (2H, dt, J=28.0, 4.0 Hz), 3.67 (2H, br).

N-(3-(2-Fluoroethoxy)phenyl)-6-fluoropyrido[3,4-d]pyrimidin-4-amine (Compound 7)

Compound 5 (0.363 mmol, 1.2 eq) was added to Compound 6 (0.303 mmol, 1.0 eq), which then was heated and refluxed in 2-propanol (2.0 mL) at 105° C. for two hours. The reaction solution was extracted with ethyl acetate and then the organic layer was collected, which was dried with sodium sulfate. Thereafter, the solvent was evaporated to dryness. The residue was purified by column chromatography and thus Compound 7 was obtained.

Yield 4.6 mg (5.0%), $^1$H NMR (400 MHz, CD$_3$OD) 8.87 (1H, s), 8.64 (1H, s), 8.03 (1H, br), 7.59 (1H, t, J=2.0 Hz), 7.40 (1H, dd, J=8.1 Hz), 7.33 (1H, t, J=8.1 Hz), 6.82 (1H, dd, J=8.1 Hz), 4.81 (H, t, J=3.8 Hz), 4.69 (1H, t, J=4.1 Hz), 4.29 (1H, t, J=4.1 Hz), 4.22 (1H, t, J=4.1 Hz).

N$^4$-(3-(2-Fluoroethoxy)phenyl)-N$^6$-(2-morpholinoethyl)pyrido[3,4-d]pyrimidine-4,6-diamine (H2)

Compound 7 (4.1 mg, 0.014 mmol) was dissolved in DMSO (900 μL) and 4-(2-amioethyl)morphorine (ALDRICH) (100 μL, 0.762 mmol) was added thereto, which then was heated at 95° C. for 20 hours. The reaction solution was extracted with ethyl acetate and then the organic layer was collected, which was dried with sodium sulfate. Thereafter, the solvent was evaporated to dryness. The residue was purified by reversed-phase HPLC and thus H2 was obtained. MHz, CDCl$_3$ 8.93 (1H, s), 8.59 (1H, s), 7.64 (1H, s), 7.32 (1H, t, J=8.4 Hz), 7.29 (1H, d, J=7.6 Hz), 6.75 (1H, d, J=7.6 Hz), 6.53 (1H, s), 4.79 (2H, dt, J=47.2, 4.0 Hz), 4.28 (2H, dt, J=28.0, 4.0 Hz), 3.78 (4H, t, J=4.4 Hz), 3.48 (2H, t, J=6.0 Hz), 2.77 (2H, t, J=6.0 Hz), 2.60 (4H, t, J=4.4 Hz).

Production Example 3

Synthesis of N$^4$-(6-fluoropyridin-3-yl)-N$^6$-(2-morpholinoethyl)pyrido[3,4-d]pyrimidin-4,6-diamine (H3)

H3 was synthesized according to the following scheme.

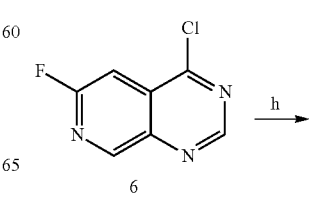

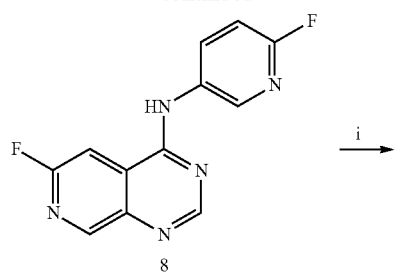

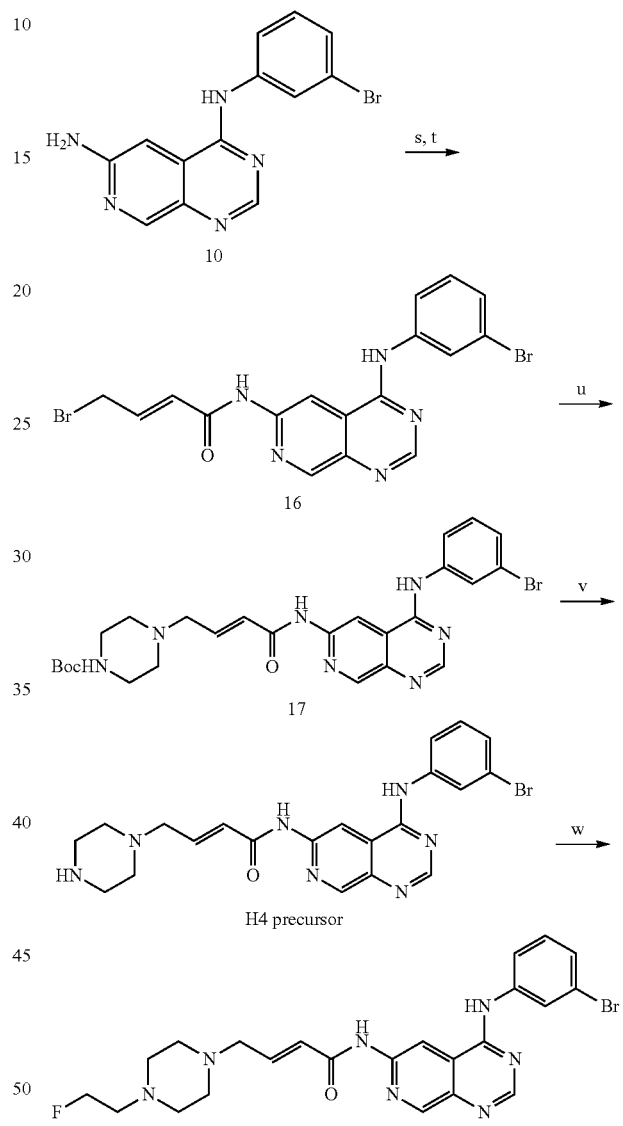

Production Example 4

Synthesis of (E)-N-(4-((3-bromophenyl)amino)pyrido[3,4-d]pyrimidin-6-yl)-4-(4-(2-fluoroethyl)piperazin-1-yl)but-2-enamide (H4)

H4 was synthesized according to the following scheme.

(s) 4-bromo-2-butenoic acid, (COCl)$_2$, DMF, CH$_2$Cl$_2$, rt, (t) N,N'-diisopropylethylamine in THF, rt; (u) N-Boc-piperazine in THF, DMF, rt; (v) TFA in THF, rt; (w) 2-fluoroethyl-4-toluene sulfonate, Et$_3$N in DMF, rt

N-(6-Fluoropyridin-3-yl)-6-fluoropyrido[3,4-d]pyrimidin-4-amine (Compound 8)

Compound 6 (0.303 mmol) and 5-Amino-2-fluoropyridine (ALDRICH) (0.363 mmol) were heated and refluxed in a 2-propanol (2.0 mL) solvent at 105° C. for two hours. The reaction solution was extracted with ethyl acetate and then the organic layer was collected, which was dried with sodium sulfate. Thereafter, the solvent was evaporated to dryness. The residue was purified by column chromatography and thus Compound 8 was obtained. Yield 20.0 mg (25.5%), $^1$H NMR (400 MHz, CDCl$_3$) 9.09 (1H, s), 8.81 (1H, s), 8.47 (1H, s), 8.44 (1H, dd, J=8.8, 2.4 Hz), 7.41 (1H, s), 7.06 (1H, dd, J=8.8, 3.2 Hz).

N$^4$-(6-Fluoropyridin-3-yl)-N$^6$-(2-morpholinoethyl)pyrido[3,4-d]pyrimidin-4,6-diamine (H3)

Compound 8 (20.0 mg, 0.077 mmol) was dissolved in DMSO (900 μL) and 4-(2-amioethyl)morphorine (ALDRICH) (100 μL, 0.762 mmol) was added thereto, which then was heated at 95° C. for 20 hours. The reaction solution was extracted with ethyl acetate and then the organic layer was collected, which was dried with sodium sulfate. Thereafter, the solvent was evaporated to dryness. The residue was purified by reversed-phase HPLC and thus H3 was obtained. Yield 14 mg (49.1%), $^1$H NMR (400 MHz, CDCl$_3$) 8.92 (1H,$), 8.61 (1H, s), 8.56 (1H, s), 8.47 (1H, m), 7.03 (1H, s), 6.99 (1H, dd, J=8.8, 3.6 Hz), 3.94 (4H, t, J=4.8 Hz), 3.74 (2H, t, J=4.8 Hz), 3.10 (2H, t, J=4.8 Hz), 3.01 (2H, m).

(2Z)—N-[4-[(3-Bromophenyl)amino]pyrido[3, 4-d]pyrimidin-6-yl]-4-bromo-2-butenamide (Compound 16)

4-Bromo-2-butenoic acid (33 mg, 0.20 mmol) was dissolved in CH$_2$Cl2 (0.5 mL), and oxalyl chloride (40 mL, 0.457 mmol) and DMF (one drop) were added thereto, which then was stirred at room temperature for one hour. The reaction solution was concentrated under vacuum. Thereafter, the residue was dissolved with THF (0.3 mL)

and then a THF solution (0.7 mL) of Compound 10 (63.2 mg, 0.100 mmol) and a THF solution (0.1 mL) of N,N'-diisopropylethylamine were added thereto, which then was stirred overnight at room temperature. After completion of the reaction, the reaction solution was poured into water and then was extracted with ethyl acetate. The organic layer thus obtained was washed with brine and then was dried with sodium sulfate. Thereafter, the solvent was evaporated to dryness. The residue thus obtained was purified by silica gel column chromatography ($CHCl_3$/MeOH=20/1) and preparative TLC ($CHCl_3$/MeOH=10/1). Yield 14.2 mg (15%), $^1$H NMR (400 MHz, DMSO-$d_6$) δ11.08 (1H, br), 10.30 (1H, br), 9.01 (1H, d, J=16.8 Hz), 8.66 (1H, s), 8.16 (1H, br), 7.89 (1H, d, J=7.7 Hz), 7.39 (1H, d, J=7.7 Hz), 7.34 (1H, dt, J=8.0, 1.8 Hz), 6.98 (1H, dt, J=15.0, 6.3 Hz), 6.68 (1H, d, J=15.0 Hz), 4.66 (2H, dd, J=6.3, 1.5 Hz).

(2Z)—N-[4-[(3-Bromophenyl)amino]pyrido[3,4-d]pyrimidin-6-yl]-4-[(4-tert-butoxycarbonyl)piperazin-1-yl]2-butenamide (Compound 17)

A THF-DMF mixed solution (2:1, 1.5 mL) of Compound 16 (19.6 mg, 0.0423 mmol) was added to a THF (2 mL) solution of N-Boc-piperazine (158 mg, 0.848 mmol), which then was stirred at room temperature for 3.5 hours. After completion of the reaction, the reaction solution was poured into a saturated sodium bicarbonate aqueous solution and then was extracted with ethyl acetate. The organic layer thus obtained was washed with water and brine sequentially and then was dried with sodium sulfate. Thereafter, the solvent was evaporated to dryness. The residue thus obtained was purified by silica gel preparative TLC ($CHCl_3$/MeOH=10/1). Yield 19.4 mg (81%), $^1$H NMR (400 MHz, DMSO-$d_6$) δ10.91 (1H, s), 10.26 (1H, br), 9.02 (1H, s), 8.98 (1H, s), 8.64 (1H, s), 8.16 (1H, br s), 7.89 (1H, br d, J=7.7 Hz), 7.39-7.32 (2H, m), 6.87 (1H, dt, J=15.4, 5.8 Hz), 6.54 (1H, d, J=15.4 Hz), 3.18 (2H, d, J=5.8 Hz), 2.50 (4H, m), 2.37 (4H, br t, J=4.8 Hz), 1.40 (9H, s).

(2Z)—N-[4-[(3-Bromophenyl)amino]pyrido[3,4-d]pyrimidin-6-yl]-4-(piperazin-1-yl)2-butenamide (H4 precursor)

TFA (500 mL) was added to a methylene chloride (1 mL) solution of Compound 17 (19.4 mg, 0.0341 mmol), which then was stirred at room temperature for 30 minutes. After completion of the reaction, the reaction solution was neutralized with a saturated sodium bicarbonate aqueous solution and then was extracted with chloroform. After the organic layer thus obtained was dried with sodium sulfate, the solvent was evaporated to dryness. The residue thus obtained was purified by amino-silica gel preparative TLC ($CHCl_3$/MeOH=20/1). Yield 12.1 mg (76%), $^1$H NMR (400 MHz, DMSO-$d_6$) δ10.90 (1H, s), 10.28 (1H, br), 9.01 (1H, s), 8.98 (1H, s), 8.63 (1H, s), 8.15 (1H, s), 7.87 (1H, br d, J=7.4 Hz), 7.37 (1H, t, J=8.1 Hz), 7.35-7.32 (1H, m), 6.87 (1H, dt, J=15.4, 5.8 Hz), 6.53 (1H, d, J=15.4 Hz), 3.12 (2H, br d, J=5.8 Hz), 2.72 (4H, t, J=4.8 Hz), 2.33 (4H, br).

The compound (H4 precursor) thus obtained can be used as a labeling precursor.

(E)-N-(4-((3-Bromophenyl)amino)pyrido[3,4-d]pyrimidin-6-yl)-4-(4-(2-fluoroethyl)piperazin-1-yl)but-2-enamide (H4)

After the H4 precursor (17.5 mg, 0.0374 mmol) was dissolved in anhydrous DMF (0.75 mL), $Et_3N$ (16 µL, 0.115 mmol) and 2-fluoroethyl 4-toluene sulfonate (16.8 mg, 0.0770 mmol) were added thereto, which then was stirred at room temperature for five days. The reaction solution was poured into a saturated sodium bicarbonate aqueous solution and then was extracted with chloroform. After the organic layer thus obtained was dried with sodium sulfate, the solvent was evaporated to dryness. The residue thus obtained was purified by amino-silica gel preparative TLC ($CHCl_3$/MeOH=20/1). Yield 8.2 mg (42.7%), $^1$H NMR (400 MHz, DMSO-$d_6$) 10.91 (1H, s), 10.27 (1H, br s), 9.02 (1H, s), 8.99 (1H, s), 8.64 (1H, br s), 8.16 (1H, br s), 7.89 (1H, br d, J=7.4 Hz), 7.34-7.37 (2H, m), 6.86 (1H, dt, J=5.9, 15.4 Hz), 6.53 (1H, d, J=15.4 Hz), 4.52 (2H, dt, J=4.4, 48.0 Hz), 3.15 (2H, d, J=5.9 Hz), 2.61 (2H, dt, J=4.4, 28.6 Hz), 2.44 (8H, m);

MS ($EI^+$) m/z: 515 ($M^{+2}$, 5), 513 ($M^+$, 5), 495 (3), 493 (3), 432 (15), 383 (100), 381 (96), 354 (40), 352 (38); HRMS ($EI^+$) m/z; 513.1286 (Calcd for $C_{23}H_{25}BrFN_7O$: 513.1288).

[Synthesis of Labeling Precursor]

A H2 precursor to serve as a labeling precursor was synthesized.

Production Example 5

Synthesis of 2-(3-((6-((2-morpholinoethyl)amino)pyrido[3,4-d]pyrimidin-4-yl)amino)phenoxy)ethyl4-methylbenzenesulfonate (H2 precursor)

A H2 precursor was synthesized according to the following scheme.

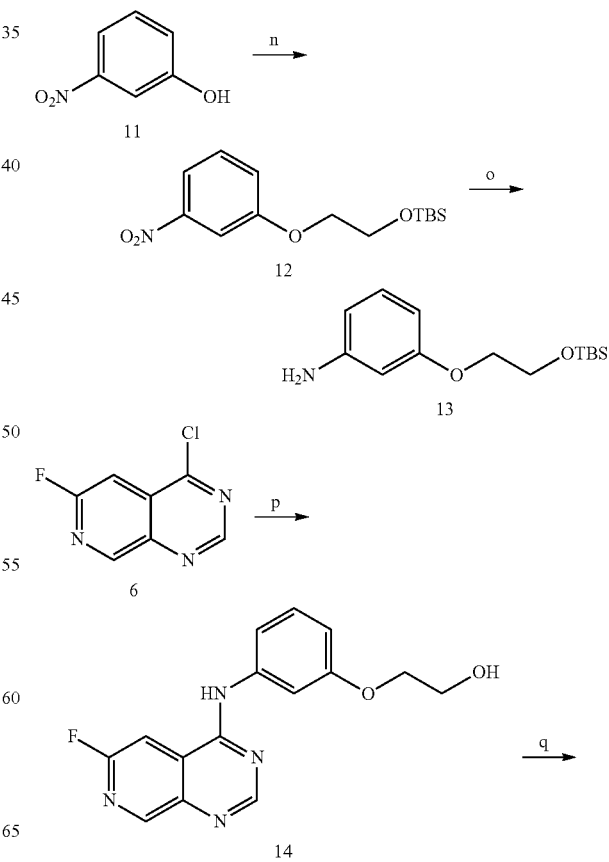

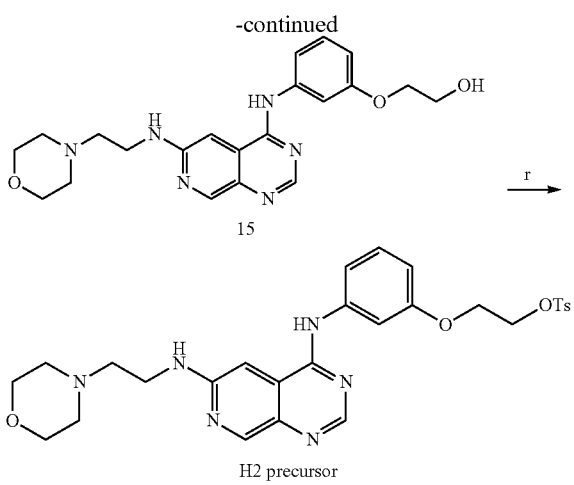

15

H2 precursor (n) (2-bromoethoxy)(tert-butyl)dimethylsilane, K2CO3 in DMF, 80° C.; (o) Pd/C, H2 in MeOH; (p) 13 in 2-propanol, reflux; (q) 4-(2-amioethyl)morphorine in DMSO, 95° C.; (r) 4-toluene sulfonylchloride, Et3N, DMAP in CH2Cl2, rt Tert-butyldimethyl(2-(3-nitrophenoxy)ethoxy)silane (Compound 12) Compound 11 (600 mg, 4.31 mmol) was dissolved in DMF (8.0 mL), and $K_2CO_3$ (1192 mg, 8.62 mmol) and (2-bromoethoxy)(tert-butyl)dimethylsilane (1118 μL, 5.17 mmol) were added thereto, which then was heated at 80° C. for 2.5 hours. The reaction solution was extracted with ethyl acetate, and the organic layer was collected and then was dried with sodium sulfate. Thereafter, the solvent was evaporated to dryness. The residue was purified by column chromatography and thus Compound 12 was obtained. Yield 1007.3 mg (78.5%), 1H NMR (400 MHz, CDCl$_3$) 7.81 (1H, d, J=8.4 Hz), 7.75 (1H, s), 7.42 (1H, t, J=8.4 Hz), 7.25 (1H, d, J=8.4 Hz), 4.13 (2H, t, J=4.8 Hz), 4.00 (2H, t, J=4.8 Hz), 0.91 (9H, s).

3-(2-((Tert-butyldimethylsilyl)oxy)ethoxy)aniline (Compound 13)

Compound 12 (1007 mg, 3.386 mmol) was dissolved in MeOH (15 mL), and Pd/C (150 mg) was added thereto, which then was reacted in an Ar gas at room temperature for 12 hours. Thereafter, the Ar gas was substituted with hydrogen and then it was stirred for two hours. After this was filtered with Hyflo Super-Cel, the solvent was evaporated to dryness. The residue was purified by column chromatography and thus Compound 13 was obtained. Yield 776.3 mg (85.7%), 1H NMR (400 MHz, CDCl$_3$) 6.94 (1H, t, J=8.0 Hz), 6.22 (1H, d, J=8.0 Hz), 6.18 (1H, d, J=8.0 Hz), 6.15 (1H, s), 3.88 (2H, d, J=4.8 Hz), 3.85 (2H, d, J=4.8 Hz), 3.54 (2H, br), 0.81 (9H, s).

2-(3-((6-Fluoropyrido[3, 4-d]pyrimidin-4-yl)amino)phenoxy)ethan-1-ol (Compound 14)

Compound 13 (243 mg, 0.908 mmol) was added to Compound 6 (111 mg, 0.606 mmol), which then was heated and refluxed in 2-propanol (4.0 mL) at 105° C. for two hours. The reaction solution was extracted with ethyl acetate and then the organic layer was collected, which was dried with sodium sulfate. Thereafter, the solvent was evaporated to dryness. The residue was purified by column chromatography and thus Compound 14 was obtained. Yield 52.8 mg (29.0%), 1H NMR (400 MHz, CD$_3$OD) 8.86 (1H, s), 8.63 (1H, s), 8.02 (1H, s), 7.57 (1H, s), 7.39 (1H, d, J=8.0 Hz), 7.31 (1H, t, J=8.0 Hz), 6.83 (1H, d, J=8.0 Hz), 4.10 (2H, t, J=4.8 Hz), 3.90 (2H, t, J=4.8 Hz).

2-(3-((6-((2-Morpholinoethyl)amino)pyrido[3,4-d]pyrimidin-4-yl)amino)phenoxy)ethan-1-ol (Compound 15)

Compound 14 (13 mg, 0.043 mmol) was dissolved in DMSO (900 μL), and 4-(2-Aminoethyl)morpholine (100 μL, 0.762 mmol) was added thereto, which then was heated at 95° C. for 20 hours. The reaction solution was extracted with ethyl acetate and then the organic layer was collected, which was dried with sodium sulfate. Thereafter, the solvent was evaporated to dryness. The residue was purified by column chromatography and thus Compound 15 was obtained. Yield 7.6 mg (42.8%), 1H NMR (400 MHz, CDCl$_3$) 8.94 (1H, s), 8.59 (1H, s), 7.64 (1H, s), 7.31 (1H, t, J=8.0 Hz), 7.23 (1H, d, J=8.0 Hz), 6.75 (1H, d, J=8.0 Hz), 6.43 (1H, s), 5.52 (1H, br), 4.15 (2H, t, J=4.0 Hz), 4.00 (2H, t, J=4.0 Hz), 3.77 (4H, m), 3.44 (2H, t, J=6.0 Hz), 2.74 (2H, t, J=6.0 Hz), 2.56 (4H, m).

2-(3-((6-((2-Morpholinoethyl)amino)pyrido[3,4-d]pyrimidin-4-yl)amino)phenoxy)ethyl4-methylbenzenesulfonate (H2 precursor)

Compound 15 (17.8 mg, 0.043 mmol) was dissolved in CH$_2$Cl2 (2.0 mL), and Et$_3$N (12.09 μL, 0.087 mmol), 4-toluenesulfonylchloride (9.09 mg, 0.048 mmol), and a catalytic amount of DMAP were added thereto at an ice-cold temperature, which then was reacted overnight at room temperature. After completion of the reaction, the reaction solution was extracted with ethyl acetate and then the organic layer was collected, which was dried with sodium sulfate. Thereafter, the solvent was evaporated to dryness. The residue was purified by column chromatography and thus an H2 precursor was obtained. Yield 2.3 mg (22.0%), 1H NMR (400 MHz, CDCl$_3$) 8.93 (1H, s), 8.58 (1H, s), 7.83 (2H, d, J=8.4 Hz), 7.52 (1H, s), 7.35 (1H, d, J=8.4 Hz), 7.32-7.26 (2H, m), 6.62 (1H, d, J=6.4 Hz), 6.50 (1H, s), 5.54 (1H, br), 4.39 (2H, t, J=4.0 Hz), 4.22 (2H, t, J=4.0 Hz), 3.77 (4H, m), 3.47 (2H, t, J=5.6 Hz), 2.76 (2H, t, J=5.6 Hz), 2.59 (4H, m), 2.44 (3H, s).

[Radiochemical Synthesis]

Radioactive labeled compounds [$^{18}$F]H2 and [$^{18}$F]H4 were synthesized.

Production Example 6

[$^{18}$F]H2 was synthesized according to the following scheme.

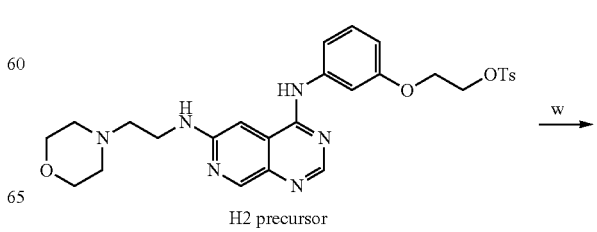

H2 precursor

-continued

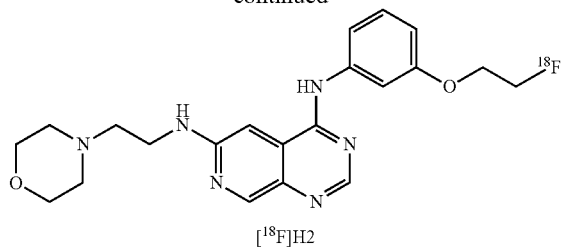

[$^{18}$F]H2

(w) [18F]KF, Kryptofix 222, K2CO3 in MeCN, 120° C., MW

N$^4$-(3-(2-[$^{18}$F]Fluoroethoxy)phenyl)-N$^6$-(2-morpholinoethyl)pyrido[3,4-d]pyrimidine-4, 6-diamine ([$^{18}$F]H2)

Kryptofix 2.2.2. (5.0 mg) and MeCN (0.5 mL) were added to a [$^{18}$F]fluoride solution (3700 MBq), which then was heated under N$_2$ stream at 120° C. to be azeotropically dehydrated. MeCN was added thereto again and azeotropic dehydration was repeated. This was dissolved in anhydrous MeCN (1.0 mL) and the H2 precursor (1.77 μmol, 1.0 mg) was added thereto, which then was reacted at 120° C. for one minute using microwaves. The reaction solution was preparatively purified by reversed-phase HPLC [COSMOSIL 5C18-AR-II, 10×250 mm, eluent 45% (C) and 55% (D), flow rate 5.0 mL/min, A=280 nm, Rt=7.6 min]. The solvent of the fraction of the target thus obtained was evaporated to dryness. Thereafter, it was dissolved in saline, which then was used for biological evaluation. The radiochemical yield was 50% and the radiochemical purity was >95%.

Production Example 7

[$^{18}$F]H4 was synthesized according to the following scheme.

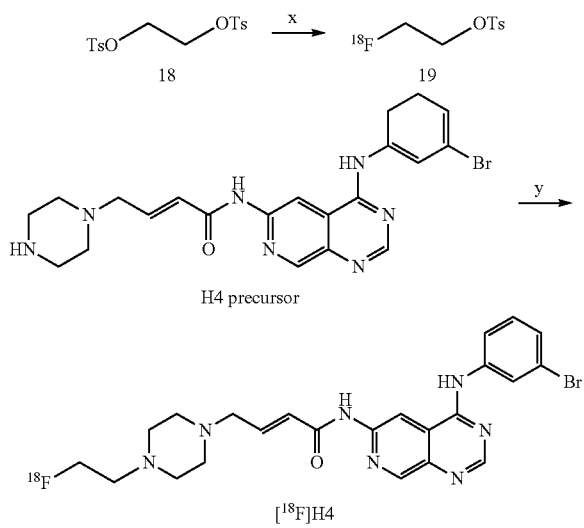

H4 precursor

[$^{18}$F]H4

(x) [18F]KF, Kryptofix 222, K2CO3 in MeCN, 90° C.; (y) 19, Et3N in DMF, 110° C.

2-[$^{18}$F]Fluoroethyl-4-toluene sulfonate (Compound 19)

Kryptofix 2.2.2. (4.50 mg) and MeCN (0.5 mL) were added to a [$^{18}$F]fluoride solution (3700 MBq), which then was heated under N$_2$ stream at 120° C. to be azeotropically dehydrated. MeCN was added thereto again and azeotropic dehydration was repeated. This was dissolved in anhydrous MeCN (0.25 mL) and ethylenglycol-1,2-ditosylate (18) (6.75 nmol, 2.50 mg) was added thereto, which then was reacted at 90° C. for five minutes. Water (0.15 mL) was added to the reaction solution, which then was preparatively purified by reversed-phase HPLC [COSMOSIL 5C18-AR-II, 10×250 mm, eluent 50% (A) and (B), flow rate 4.0 mL/min, λ=280 nm, Rt=10 to 11 min]. Water was added to the fraction of the target thus obtained to dilute it, which then was applied to Sep-Pak C18 Light Cartridge (Nihon Waters K.K.). Thereafter, water was run through it and thereby TFA was removed. The cartridge was dried under N$_2$ stream and DMF was run through it. Thus, the target was eluted.

(E)-N-(4-((3-Bromophenyl)amino)pyrido[3,4-d]pyrimidin-6-yl)-4-(4-(2-[$^{18}$F]fluoroethyl)piperazin-1-yl)but-2-enamide ([$^{18}$F]H4)

The H4 precursor (1.07 μmol, 0.50 mg) was dissolved in anhydrous DMF (20 μL), which then was added to a DMF solution (100 μL) of Compound 19. Furthermore, Et$_3$N (1.45 μL) was added thereto, which then was reacted at 110° C. for 20 minutes. The reaction solution was preparatively purified by reversed-phase HPLC [COSMOSIL 5C18-AR-II, 10×250 mm, gradient of 80:20 (0 min)→60:40 (20 min) by (A) and (B), flow rate 5.0 mL/min, λ=280 nm]. Water was added to the fraction of the target thus obtained to dilute it, which then was applied to Sep-Pak C18 Light Cartridge. Thereafter, water was run through it and thereby TFA was removed. The solvent was evaporated to dryness and then it was dissolved in 1% Tween saline. This was used for the biological evaluation. The radiochemical yield was 3.8% and the radiochemical purity was >95%.

[EGFR Tyrosine Kinase Inhibiting Activity Measurement 1]

The inhibiting activity of each Compound (H1 to H4) and gefitinib with respect to EGFR tyrosine kinase was measured using EGFR Kinase Enzyme Systems (Promega) and ADP-Glo™ Kinase assay Kit (Promega, Catalog No. V9101).

Four types of EGFR Kinase Enzyme Systems, specifically, EGFR Kinase Enzyme System (Catalog No. V3831), EGFR (L858R) Kinase Enzyme System (Catalog No. V5322), EGFR (T790M) Kinase Enzyme System (Catalog No. V4506), and EGFR (T790M, L858R) Kinase Enzyme System (Catalog No. V5324) were used (all of them were manufactured by Promega).

The measurement was carried out according to the Promega protocol applications guide. That is, a buffer solution (40 mM Tris-HCl, pH 7.5, 20 mM MgCl$_2$, 50 μM DTT and 0.1 mg/mL BSA) was used as a dilute solution. The concentration of each compound started at 100 μM (the final concentration, including 1% DMSO) with 5-fold dilutions with the buffer solution. Thus, ten concentrations of each compound were prepared. The initial concentration of PD158780 alone was set at 10 μM (the final concentration, including 1% DMSO) but it was prepared in the same manner as the compound group. Then, 2 μL of each concentration of each compound thus obtained was added to each well of a 384-well plate. Furthermore, 4 μL (20 ng) of an EGFR Kinase Buffer that came with each EGFR Kinase Enzyme System was added to each well, which then was incubated at room temperature for ten minutes. Subsequently, 4 μL of mixed solution of ATP (10 μM) and Poly(Glu, Tyr) (2 μg) substrate was added to each well, which then was incubated at room temperature for one hour. Then, 10 μL of ADP-Glo™ Reagent (ADP-Glo™ Kinase Assay, Promega) was added to each well, which then was reacted at room temperature for 40 minutes. Furthermore, 20 μL of Kinase Detection Reagent (ADP-Glo™ Kinase Assay, Promega) was added to each well, which then was reacted at room temperature for one hour. Thereafter, the amount of luminescence was measured using Luminescence Counter 1420 ARVO™ Light (PerkinElmer Japan Co., Ltd.). From the data thus obtained, dose-response curves and $IC_{50}$ were calculated using GraphPad Prism 5 (GraphPad Software, Inc.). The results are shown in Table 1 below. In Table 1 below, WT indicates the measurement results obtained with the EGFR Kinase Enzyme System, L858R indicates the measurement results obtained with the EGFR (L858R) Kinase Enzyme System, T790M indicates the measurement results obtained with the EGFR (T790M) Kinase Enzyme System, and DM indicates the measurement results obtained with the EGFR (T790M, L858R) Kinase Enzyme System.

As shown in Table 1, H1 to H4 each showed a relatively high binding affinity to the L858R-mutated EGFR but showed no binding affinity to the L858R/T790M-mutated EGFR (DM in Table 1). Furthermore, H2 showed a relatively high binding affinity to the L858R-mutated EGFR but had a low binding affinity to the wild-type EGFR and showed no binding affinity to the L858R/T790M-mutated EGFR.

[EGFR Tyrosine Kinase Inhibiting Activity Measurement 2]

EGFR Tyrosine Kinase Inhibiting Activity Measurement 2 was carried out in the same manner as in EGFR Tyrosine Kinase Inhibiting Activity Measurement 1 except that Compound H4, erlotinib, and AZD9291 were used and the incubation was carried out for two hours after ATP and Poly(Glu, Tyr) substrate were added. The results are shown in Table 2 below. AZD9291 is a compound that is considered to have an inhibitory effect on both L858R-mutated EGFR-TK and L858R/T790M-mutated EGFR-TK.

TABLE 1

| | | | | EGFR Kinase inhibition: $IC_{50}$ (μM) | | | |
|---|---|---|---|---|---|---|---|
| | $R_1$ | $L_1$ | $R_2$ | WT | L858R | T790M | DM |
| H1 | F— | —CH₂CH₂— | 3-Br-phenyl | 0.017 | 0.015 | 4.112 | 4.018 |
| H2 | morpholino | —CH₂CH₂— | 3-(OCH₂CH₂F)-phenyl | 7.206 | 0.653 | >10 | >10 |
| H3 | morpholino | —CH₂CH₂— | 6-F-pyridin-3-yl | 3.753 | 0.686 | >10 | >10 |
| H4 | 4-(2-fluoroethyl)piperazin-1-yl | —CH₂CH=CH—C(O)— | 3-Br-phenyl | 0.049 | 0.058 | 0.409 | 0.406 |
| PD158780 | | | | 0.006 | | | |
| Gefitinib | | | | 0.021 (0.036) | 0.011 (0.015) | 0.634 (0.835) | 4.540 (8.125) |

>10: <50% enzyme inhibition at 10 μM.

TABLE 2

| EGFR Kinase Inhibition: IC$_{50}$ [nM] | | |
|---|---|---|
| | L858R | L858R/T790M |
| H4 | 15.6 ± 0.8 | 326 ± 64 |
| Erlotinib | 12.5 ± 6.0 | 4040 ± 1270 |
| AZD9291 | 12.3 ± 3.1 | 14.5 ± 5.3 |

>10,000:<50% enzyme inhibition at 10 μM

As shown in Table 2, H4 exhibited a relatively high binding affinity to the L858R-mutated EGFR. The binding affinity to the L858R-mutated EGFR of H4 was comparable to those of erlotinib and AZD9291. On the other hand, the binding affinity to the L858R/T790M-mutated EGFR of H4 was lower than AZD9291 and was higher than Erlotinib. This suggested that H4 binds specifically to L858R-mutated EGFR.

[Cell Culture and Model Mouse]

Two types of EGFR mutation-positive human non-small cell lung cancer cells H3255 (L858R mutation) and H1975 (L858R/T790M mutation) were cultured in a DMEM/Ham's F-12 medium (Nacalai Tesque) containing glutamine, antibiotics (penicillin-streptomycin), and 20% fetal bovine serum.

$1\times10^7$ cells/mouse of H3255 cells suspended in BD Matrigel™ Basement Membrane Matrix was implanted to the right shoulder of a 5-week-old male BALB/c nu/nu mouse (Shimizu Laboratory Supplies), and thereby a tumor-bearing mouse was prepared. They were used for experiments, with the tumor being 1 cm or smaller in diameter.

[Cellular Uptake Inhibition Experiment 1]

The binding specificity of H4 to each mutated EGFR-TK was evaluated by a cellular uptake inhibition experiment using H3255 cells, which are L858R mutant cells, and H1975 cells, which are L858R/T790M mutant cells. H3255 and H1975 cells ($4\times10^5$ cells/well) were cultured in a 12-well plate for 48 hours. After the medium was removed, each well was washed with PBS(−) once. Each fetal bovine serum-free DMEM/Ham's F-12 medium with [$^{18}$F]H4 (0.15 MBq/mL) and gefitinib (0, 0.5, 1, and 2.5 μM) added thereto was added to each well, which then was incubated in a CO$_2$ incubator for two hours. Each well was washed with 0.1% Tween 80/1% DMSO/PBS(−) three times, and the cells were dissolved with 0.2 N NaOH. The radioactivity of each solution was measured with the gamma counter, and the protein concentration was determined using a BCA Protein Assay Kit (Pierce, Rockford, Ill.) and then the measurement results were analyzed. FIG. 1 shows the results.

As shown in FIG. 1, the uptake of [$^{18}$F]H4 into the H3255 cells was inhibited by gefitinib, which is an EGFR-TKI. On the other hand, the uptake of [$^{18}$F]H4 into the H1975 cells was approximately 50% ID/mg protein regardless of the presence or absence of gefitinib added thereto and the concentration thereof. This suggested the possibility that [$^{18}$F]H4 could discriminate L858R-mutated EGFR with an L858R mutation (a primary mutation) introduced thereinto from L858R/T790M-mutated EGFR with a T790M mutation (a secondary mutation) introduced thereinto, which emerged following the primary mutation.

[Cellular Uptake Inhibition Experiment 2]

Figure 2:
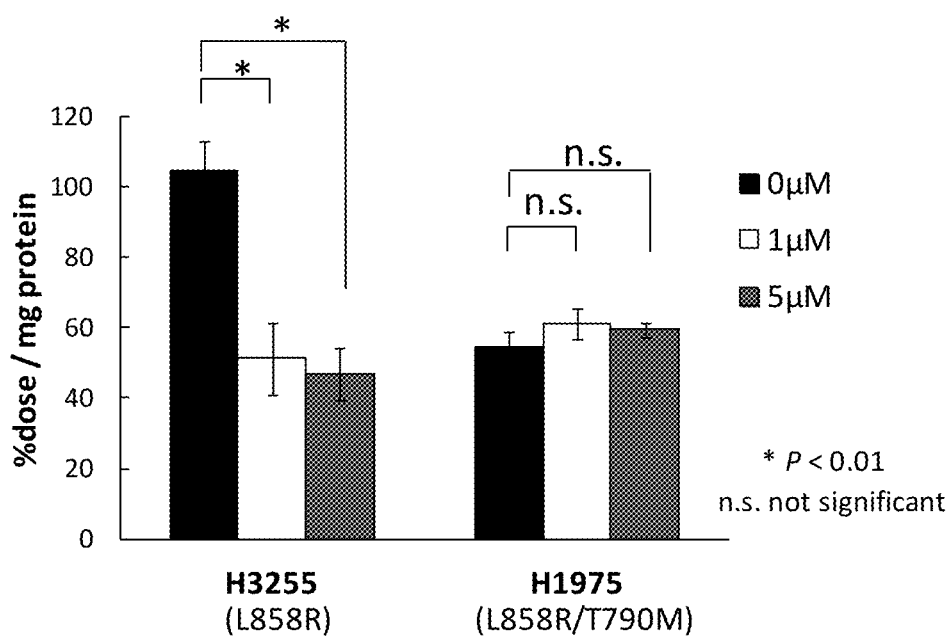
FIG. 2 is a graph showing an example of the results of Experiment 2 on the cellular uptake of [$^{18}$F]H4 using H3255 cells and H1975 cells.

H3255 and H1975 cells ($4\times10^5$ cells/well) were cultured in a 12-well plate for 24 hours. After the medium was removed, each well was washed with PBS(−) once. Each fetal bovine serum-free DMEM/Ham's F-12 medium with AZD9291 (0, 1, and 5 μM) added thereto was added to each well, which then was incubated in a 5% CO$_2$ incubator at 37° C. for 30 minutes. [$^{18}$F]H4 (148 kBq/well) was added to each well, which then was incubated in the 5% CO$_2$ incubator at 37° C. for two hours. Each well was washed with 0.1% Tween 80/1% DMSO/PBS(−) three times, and the cells were dissolved with 0.2 N NaOH. The radioactivity of each solution was measured with the gamma counter and the protein concentration was determined using the BCA Protein Assay Kit (Pierce, Rockford, Ill.) and then the measurement results were analyzed. FIG. 2 shows the results.

As shown in FIG. 2, the uptake of [$^{18}$F]H4 into the H3255 cells was inhibited by AZD9291, which is an EGFR-TKI. On the other hand, the uptake of [$^{18}$F]H4 into the H1975 cells was approximately 50% ID/mg protein regardless of the presence or absence of AZD9291 added thereto and the concentration thereof. This suggested the possibility that [$^{18}$F]H4 binds specifically to L858R-mutated EGFR and [$^{18}$F]H4 could discriminate L858R-mutated EGFR from L858R/T790M-mutated EGFR.

Biodistribution Experiment

Figure 3:
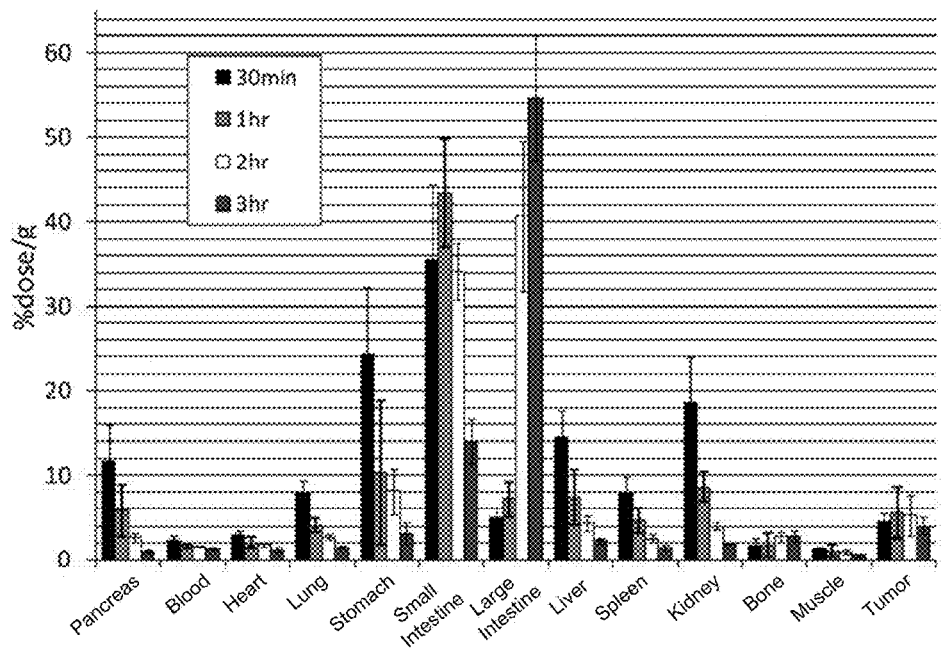
FIG. 3 is a graph showing an example of variations with time of biodistribution using [$^{18}$F]H4.

[$^{18}$F]H4 was dissolved in saline containing 0.1% Tween 80 so as to be 6 μCi/100 μL and 100 μL thereof was administered to each tumor-bearing mouse through a tail vein. The mice were decapitated/slaughtered at predetermined time points (30 minutes, 1 hour, 2 hours, and 3 hours after administration). The blood was collected and tissues were removed and then the mass and the accumulated radioactivity were measured. The amount of accumulation (% dose/g) was calculated from the radioactivity per unit weight and the accumulation in the tissues was evaluated. The results are shown in FIG. 3 and Table 3 below. FIG. 3 is a graph showing an example of variations with time of the accumulation of [$^{18}$F]H4 in each organ. Table 3 below shows the tumor/blood ratio (the amount of accumulation in the tumor/the amount of accumulation in the blood) and the tumor/muscle ratio (the amount of accumulation in the tumor/the amount of accumulation in the muscle).

TABLE 3

| | Time After Administration | | | |
|---|---|---|---|---|
| | 30 min | 60 min | 120 min | 180 min |
| Tumor/Blood Ratio | 1.99 | 3.24 | 3.28 | 3.03 |
| | (0.08) | (1.81) | (1.41) | (0.60) |
| Tumor/Muscle Ratio | 3.47 | 8.89 | 5.75 | 9.29 |
| | (0.24) | (6.93) | (2.52) | (3.69) |

Each point is the average value (SD) of 5 mice.

The accumulation of [$^{18}$F]H4 in each organ was checked from 30 min to 180 min after administration and as shown in Table 3, the tumor/blood ratio was around 3 while the tumor/muscle ratio varied but exceeded 5. Thus, good results were obtained. The results suggested the possibility that [$^{18}$F]H4 could be used to image L858R-mutated EGFR. Furthermore, a rapid transition from the liver to the intestine was observed and thus, it was found to be quickly metabolized and excreted.

Biodistribution Experiment (Blocking Experiment)

[$^{18}$F]H4 (222 kBq) and AZD9291 (17 μg) were administered to each H3255 tumor-bearing mouse through a tail vein. At 180 minutes after the administration, they were slaughtered and H3255 tumor tissues were removed. The mass and the accumulated radioactivity were measured, and the amount of accumulation (% dose/g) was calculated from the radioactivity per unit weight. This was carried out in the same manner as above except that AZD9291 was not administered.

Furthermore, this experiment was carried out in the same manner as above except that H1975 tumor-bearing mice were used.

Figure 4:
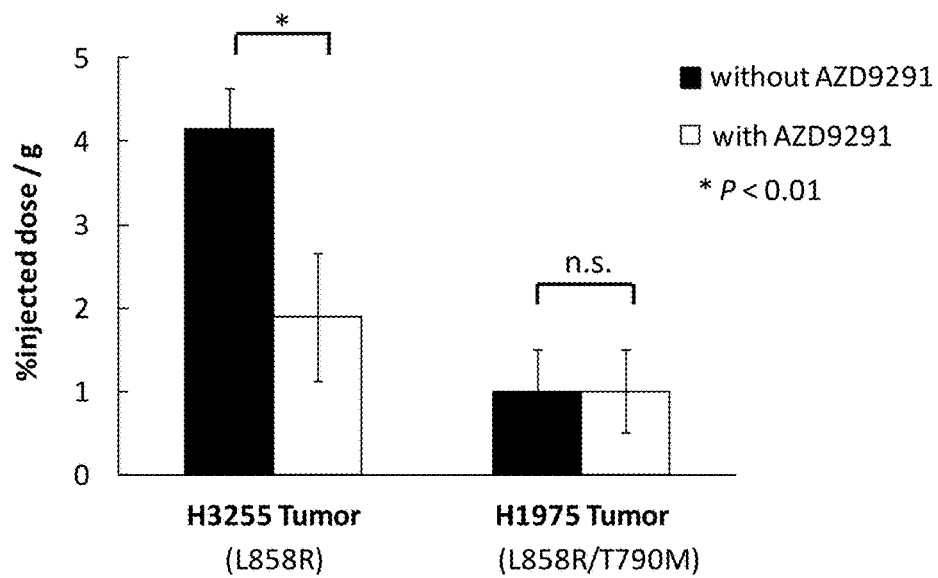
FIG. 4 is a graph showing an example of the results of biodistribution of [$^{18}$F]H4 using a H3255 tumor-bearing mouse and a H1975 tumor-bearing mouse (a blocking experiment).

These results are shown in FIG. 4.

In FIG. 4, the result of the H3255 tumor-bearing mice is shown on the left side and the result of the H1975 tumor-bearing mice is shown on the right side. As shown in FIG. 4, in the H1975 tumor (L858R/T790M mutation), the accumulation of [$^{18}$F]H4 hardly changed regardless of the presence or absence of administration of AZD9291. On the other hand, in the H3255 tumor (L858R mutation), AZD9291 administered simultaneously resulted in a reduction in accumulation of [$^{18}$F]H4 by at least half the accumulation (54%). This suggested the possibility that [$^{18}$F]H4 binds specifically to L858R-mutated EGFR and [$^{18}$F]H4 can discriminate L858R-mutated EGFR from L858R/T790M-mutated EGFR.

[PET/CT Imaging 1]

[$^{18}$F]H4 (9.8 MBq/150 μL) was administered to a H3255 tumor-bearing mouse through a tail vein. He was anesthetized by inhalation of isoflurane (2.0%) from 175 minutes after the administration and then was imaged for 20 minutes from 180 minutes after the administration using a PET/CT device (FX-3300). Thereafter, CT imaging (60 kV, 320 μA) was carried out. The image reconstruction was carried out using 3D-OSEM.

Figure 5:
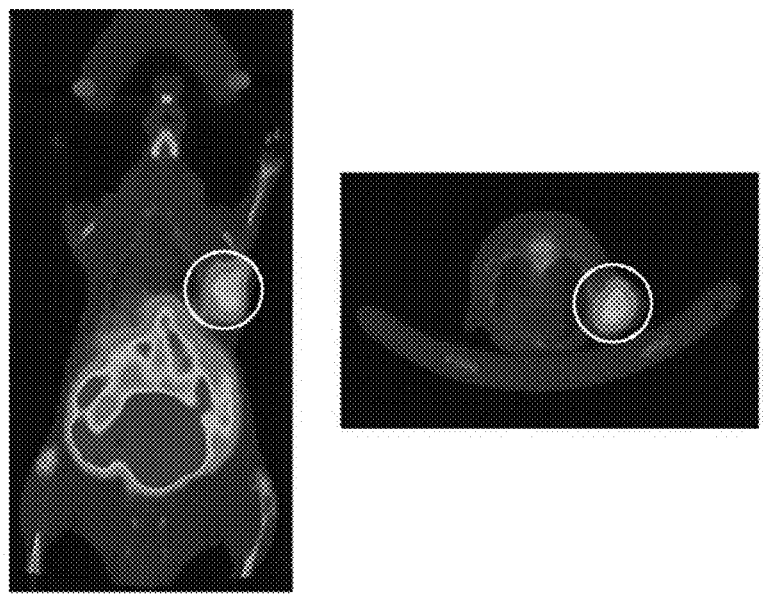
FIG. 5 shows images of an example of the results of PET/CT imaging of a H3255 tumor-bearing mouse using [$^{18}$F]H4.

<Imaging Conditions>
Animal: Balb/c nu/nu mouse, 10 w, male, 22.2 g
Cell: H3255 (1×10$^7$ cells/100 μL)
Injection dose: 264 μCi/150 μL
PET/CT: FX-3300 (GMI)
Image acquisition: 180 to 200 min after administration
Reconstruction: 3D-OSEM
Condition of CT: 60 kV, 320 μA Images acquired by the imaging are shown in FIG. 5. In FIG. 5, the left image is a coronal view and the right image is a transverse view. In FIG. 5, the circled portion is the portion with H3255 implanted thereto. As shown in FIG. 5, [$^{18}$F]H4 was accumulated specifically in the portion where H3255 was implanted, and thus [$^{18}$F]H4 allowed the L858R-mutated EGFR to be imaged.

[PET/CT Imaging 2]

PET/CT Imaging 2 was carried out in the same manner as in PET/CT Imaging 1 except that a H1975 tumor-bearing mouse was used and the following imaging conditions were employed.

Figure 6:
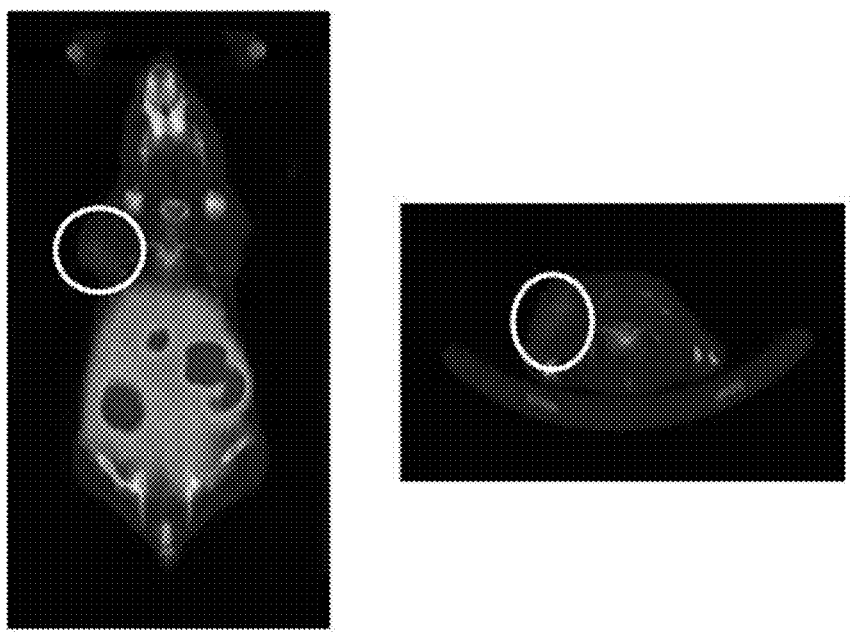
FIG. 6 shows images of an example of the results of PET/CT imaging of a H1975 tumor-bearing mouse using [$^{18}$F]H4.

<Imaging Conditions>
Animal: Balb/c nu/nu mouse, 9 w, male, 20.9 g
Cell: H1975 (3×10$^6$ cells)
Injection dose: 486 μCi/150 μL
PET/CT: FX-3300 (GMI)
Image acquisition: 180 to 200 min after administration
Reconstruction: 3D-OSEM
Condition of CT: 60 kV, 320 μA Images acquired by the imaging are shown in FIG. 6. In FIG. 6, the left image is a coronal view and the right image is a transverse view. In FIG. 6, the circled portion is the portion with H1975 implanted thereto. As shown in FIG. 6, no specific accumulation of [$^{18}$F]H4 was observed in the portion with H1975 implanted thereto.

The results of the PET/CT imaging described above showed that imaging using [$^{18}$F]H4 allows an EGFR gene in a cancer tissue (a tumor) to be determined to be L858R-mutated or L858R/T790M-mutated. Thus, the imaging allowed to determine whether a secondary mutation was developed or not and whether it had EGFR-TKI resistance or not.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A nuclear medicine diagnostic imaging agent, comprising a compound represented by Formula (1) or a pharmaceutically acceptable salt thereof,

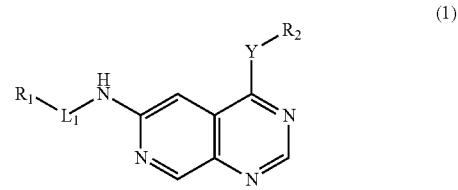

wherein:
$L_1$ is an alkanediyl group having 1 to 5 carbon atoms or an alkenediyl carbonyl group having 3 to 8 carbon atoms;
$R_1$ is a radioactive halogen atom, or a 5- to 7-membered monocyclic nitrogen-containing heterocycloalkyl optionally substituted with one substituent;
$R_2$ is a 6- to 8-membered aryl group or a nitrogen-containing heteroaryl group with one substituent;
the substituents of $R_1$ and $R_2$ are each independently a halogen atom, an alkyl group having 1 to 5 carbon atoms, a halogenated alkyl group having 1 to 5 carbon atoms, or a —(CH$_2$)$_l$(O—C$_2$H$_4$)$_m$—X$_1$ group;
l is 0 to 5;
m is 0 to 5;
$X_1$ is a radioactive halogen atom or —[$^{11}$C]CH$_3$;
either $R_1$ or $R_2$ contains a radioactive halogen atom or a radioactive carbon atom ($^{11}$C); and
Y is —NH— or —O—.

2. The nuclear medicine diagnostic imaging agent according to claim 1, wherein $L_1$ is —(CH$_2$)$_2$— or —(C=O)—CH=CH—CH$_2$—.

3. The nuclear medicine diagnostic imaging agent according to claim 1, wherein $R_1$ is

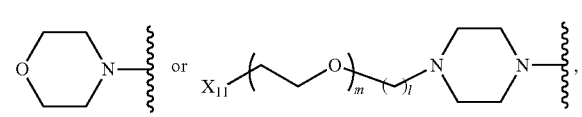

wherein l is 0 or 2, m is 0 to 5, and $X_1$ is a radioactive halogen atom or —[$^{11}$C]CH$_3$.

4. The nuclear medicine diagnostic imaging agent according to claim 1, wherein $R_2$ is

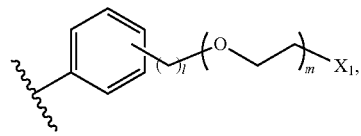

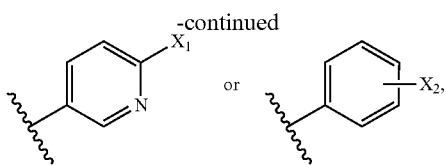

wherein l is 0 or 2, m is 0 to 5, $X_1$ is a radioactive halogen atom or —[$^{11}$C]CH$_3$, and $X_2$ is a halogen atom.

5. A compound represented by Formula (1) or a pharmaceutically acceptable salt thereof,

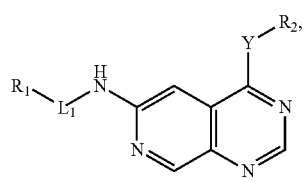

(1)

wherein:

$L_1$ is an alkanediyl group having 1 to 5 carbon atoms or an alkenediyl carbonyl group having 3 to 8 carbon atoms;

$R_1$ is a radioactive halogen atom, or a 5- to 7-membered monocyclic nitrogen-containing heterocycloalkyl optionally substituted with one substituent;

$R_2$ is a 6- to 8-membered aryl group or nitrogen-containing heteroaryl group with one substituent;

the substitutents of $R_1$ and $R_2$ are each independently a halogen atom, an alkyl group having 1 to 5 carbon atoms, a halogenated alkyl group having 1 to 5 carbon atoms, or a —(CH$_2$)$_l$—(O—C$_2$H$_4$)$_m$—X$_1$ group;

l is 0 to 5, m is 0 to 5;

$X_1$ is a radioactive halogen atom or —[$^{11}$C]CH$_3$;

either $R_1$ or $R_2$ contains a radioactive halogen atom or a radioactive carbon atom ($^{11}$C); and Y is —NH— or —O—.

* * * * *